(12) United States Patent
Creighton et al.

(10) Patent No.: US 7,700,560 B2
(45) Date of Patent: Apr. 20, 2010

(54) INACTIVATORS AND BIVALENT INHIBITORS OF GLYOXALASE I AND METHODS OF INHIBITING TUMOR GROWTH

(75) Inventors: Donald J. Creighton, Baltimore, MD (US); Zhe-Bin Zheng, Shanghai (CN)

(73) Assignee: University of Maryland, Baltimore County, Baltimore, MD (US)

( * ) Notice: Subject to any disclaimer, the term of this patent is extended or adjusted under 35 U.S.C. 154(b) by 821 days.

(21) Appl. No.: 10/559,410

(22) PCT Filed: May 28, 2004

(86) PCT No.: PCT/US2004/014535

§ 371 (c)(1),
(2), (4) Date: May 18, 2006

(87) PCT Pub. No.: WO2005/007079

PCT Pub. Date: Jan. 27, 2005

(65) Prior Publication Data

US 2007/0129311 A1 Jun. 7, 2007

Related U.S. Application Data

(60) Provisional application No. 60/475,946, filed on Jun. 5, 2003.

(51) Int. Cl.
*A61K 38/08* (2006.01)
*C07K 5/02* (2006.01)
*C07K 5/08* (2006.01)
*C07K 5/10* (2006.01)

(52) U.S. Cl. .................. 514/17; 530/330; 530/331; 530/332

(58) Field of Classification Search .................. None
See application file for complete search history.

(56) References Cited

U.S. PATENT DOCUMENTS 5,616,563 A * 4/1997 Creighton et al. .............. 514/18
5,969,174 A * 10/1999 Creighton et al. ........... 558/232
6,395,266 B1 * 5/2002 Martinez et al. ........... 424/78.3

FOREIGN PATENT DOCUMENTS

WO  WO 9600061 A1 * 1/1996
WO  WO 9935128 A1 * 7/1999

OTHER PUBLICATIONS

KK Bhargava et al. J. Am. Chem. Soc. (1983) 105(10), pp. 3247-3251.*
Kalsi, A., et al., "Role of Hydrophobic Interactions in Binding S-(N-Aryl/Alkyl-N-hydroxy-carbamoyl)glutathiones to the Active Site of the Antitumor Target Enzyme Glyoxalase I," *J. Med. Chem.*, 2000, 43, 3981-3986.
Kavarana, M.I., et al., "Mechanism-Based Competitive Inhibitors of Glyoxalase I: Intracellular Delivery, in vitro Antitumor Activities, and Stabilities in Human Serum and Mouse Serum," *J. Med. Chem.*, 1999, 42, 221-228.
Creighton, D.J., "Glyoxalase I inhibitors in Cancer Checmotherapy," *Biochem. Society Transactions*, 2003, vol. 21, part 6, 1378-1382.
Cameron, A.D., et al., "Reaction Mechanism of Glyoxalase I Explored by an X-ray Crystallographic Analysis of the Human Enzyme in Complex with a Transition State Analogue," *Biochemistry*, 1999, 38, 13480-13490.
Burg, *Drug Metabolism Reviews*, 34(4):821-863 (2002).
Zheng, *Organic Letters*, 4(25):4855-4858 (2003).
Himo, *J. Am. Chem. Soc.*, 123:10280-10289 (2001).

* cited by examiner

*Primary Examiner*—Andrew D Kosar
(74) *Attorney, Agent, or Firm*—Sughrue Mion, PLLC

(57) ABSTRACT

Compounds comprising two human GlxI inhibitors covalently linked via a chemical linker are provided, wherein each of said two human GlxI inhibitors, which may be the same or different, is an S-substituted glutathione or an S-substituted glutathione prodrug, wherein said GlxI inhibitors each have a γ-glutamyl amino group, wherein said chemical linker is covalently bound to each GlxI inhibitor via said γ-glutamyl amino group, and wherein said chemical linker has a length of at least 50 Angstroms. Monovalent irreversible inactivators of human GlxI are also provided. An antineoplastic composition is provided, which comprises a compound described above and a pharmaceutically acceptable carrier. In vitro and in vivo methods of preventing or inhibiting the growth and proliferation of neoplastic cells and/or tumors are also provided.

28 Claims, 8 Drawing Sheets

INACTIVATORS AND BIVALENT INHIBITORS OF GLYOXALASE I AND METHODS OF INHIBITING TUMOR GROWTH

CROSS-REFERENCE TO RELATED APPLICATION

This application is a 371 of PCT/US2004/014535, filed May 28, 2004; which claims benefit of Provisional Application No. 60/475,946, filed Jun. 5, 2003; the disclosure of each of which is incorporated herein by reference.

GOVERNMENT RIGHTS

This invention was created in part using funds from the federal government under a grant from the National Institutes of Health (CA 59612). The United States Government, therefore, has certain rights in this invention.

FIELD OF INVENTION

This invention relates to small molecule, chemotherapeutic agents having antitumor activity and methods for administrating these agents to humans. Specifically, this invention relates to, inter alia, the development and use of small molecule, chemotherapeutic agents that target the active site of the methylglyoxal-detoxifying enzyme glyoxalase I causing tumor regression, and methods for administering these compounds to humans to inhibit tumor cell growth.

BACKGROUND OF THE INVENTION

Recent advances in understanding the metabolism of methylglyoxal in mammalian cells suggest that the glutathione (GSH)-dependent glyoxalase enzyme system is a useful target for antitumor drug development (Creighton et al, *Drugs of the Future*, 25:385-392 (2000)). The physiological function of this detoxification pathway is to remove cytotoxic methylglyoxal from cells as D-lactate via the sequential action of the isomerase glyoxalase I (GlxI) and the thioester hydrolase glyoxalase II (GlxII), as shown in Scheme 1 below (Creighton et al, "Glutathione-Dependent Aldehyde Oxidation Reactions", *In Molecular Structure and Energetics: Principles of Enzyme Activity*, Liebman et al, Eds.; VCH Publishers, 9: 353-386 (1988)).

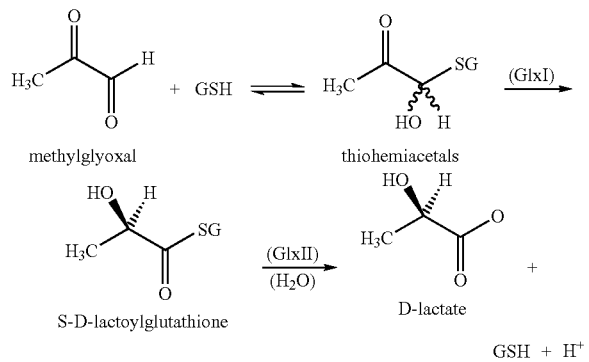

Methylglyoxal is a highly reactive alpha-ketoaldehyde that arises as a normal by-product of carbohydrate metabolism (Richard et al, *Biochemistry*, 30:4581-4585 (1991)) and is capable of covalently modifying proteins and nucleic acids critical to cell viability (Reiffen et al, *J. Cancer Res. Clin. Oncol.*, 107:206-219 (1984); Ayoub et al, *Leuk. Res.*, 17:397-401 (1993); Baskaran et al, *Biochem. Int.*, 212:166-174 (1990); Ray et al, *Int. J. Cancer*, 47:603-609 (1991); White et al, *Chem-Biol. Interact.*, 38:339-347 (1982); and Papoulis et al, *Biochemistry*, 34:648-655 (1995)).

Inhibitors of GlxI have long been sought as possible anticancer agents, because of their potential ability to induce elevated concentrations of methylglyoxal in tumor cells (Creighton et al (2000), supra), and because of the observation that rapidly dividing tumor cells are exceptionally sensitive to the cytotoxic effects of exogenous methylglyoxal (Ray et al, supra; White et al, supra; and Papoulis et al, supra). The basis of this sensitivity is not well understood, but appears to arise, in part, from methylglyoxal induced activation of the stress-activated protein kinases c-Jun $NH_2$-terminal kinase 1 (JNK1) and p38 mitogen-activated protein kinase (MAPK), which leads to caspase activation and apoptosis (programmed cell death) in tumor cells (Sakamoto et al, *Clinical Cancer Research*, 7:2513-2518 (2001); and Sakamoto et al, *J. Biol. Chem.*, 277:45770-45775 (2002)). Moreover, methylglyoxal is probably genotoxic, on the basis of its ability to covalently modify nucleotide bases in DNA (Papoulis et al, supra).

Further, inhibitors of hGlxI that are hydrolytically destroyed by the thioester hydrolase GlxII offer a selective strategy for specifically inhibiting tumor cells, as normal cells contain much higher concentrations of GlxII than tumor cells. Table 1 below shows a comparison of the activities of GlxI and GlxII in normal versus cancer cells (Creighton et al (2000), supra).

TABLE 1

Reported Glyoxalase Activities in Normal Cells versus Cancer Cells

| Tissue | Glyoxalase Activity (mU/mg protein) | | GlxI/GlxII |
| --- | --- | --- | --- |
| | GlxI | GlxII | |
| Normal | | | |
| brain (human) | 1113 ± 19 | 817 ± 156 | 1.4 |
| liver (human) | 209 ± 56 | 360 ± 13 | 0.6 |
| heart (hamster) | 339 ± 24 | 280 ± 47 | 1.2 |
| kidney (human) | 323 ± 48 | 330 ± 86 | 1.0 |
| lymphocytes (mouse) | 360 ± 30 | 200 ± 30 | 1.8 |
| Tumor | | | |
| melanoma B16 (mouse) | 370 ± 160 | 66 ± 18 | 5.6 |
| leukemia L1210 (mouse) | 310 ± 30 | 20 ± 3 | 15.5 |
| glioblastoma (human) | 290 ± 56 | 53 ± 10 | 5.5 |
| fibroadenoma mammae (human) | 419 ± 73 | 27 ± 7 | 15.5 |
| bladder HT-1107 (human) | 542 ± 38 | 8 ± 1 | 67.8 |
| prostate PC-3 (human) | 4206 ± 294 | 45 ± 3 | 93.4 |
| testis T1 (human) | 4767 ± 275 | 94 ± 12 | 51.0 |
| colon HT29 (human) | 542 ± 59 | 11 ± 1 | 49.3 |

Thus, normal cells should be able to detoxify thioester inhibitors of hGlxI much more rapidly than the corresponding tumor cells, resulting in much higher steady concentrations of the inhibitors in tumor cells. Consistent with this hypothesis, the diethylester prodrug form of S—(N-p-chlorophenyl-N-hydroxycarbamoyl) glutathione (CHG), which is both an inhibitor of hGlxI and a substrate for hGlxII (Murthy et al, *J. Med. Chem.*, 37:2161 (1994)), is significantly more toxic to murine leukemia L1210 cells than to normal splenic lymphocytes in culture, reflecting the 10-fold lower activity of hGlxII in L1210 cells versus splenic lymphocytes (Kavarana et al, *J. Med. Chem.*, 42:221-228 (1999)).

Since an ideal chemotherapeutic agent should be highly specific for cancer cells and therefore have minimal side effects, GlxI inhibitors are attractive anticancer agents because of their selective accumulation in tumor cells rather than normal cells.

Further, an antitumor strategy targeting hGlxI provides benefits over more established chemotherapies that attack rapidly dividing tumor cells at various stages of mitosis, or that arrest tumor cells at some stage in the cell cycle. For example, many of the small molecule antitumor drugs currently in use target rapidly dividing tumor cells by either directly or indirectly inhibiting DNA and/or protein synthesis. Thus, these drugs will also adversely affect rapidly dividing normal cells, like those of the intestinal epithelium and bone marrow. As a result, side-effects of antitumor agents currently in use often include myelosuppression, intestinal disorders, dose-dependent cardiotoxicity, pulmonary fibrosis, anaphylactic reactions, alopetia, and anorexia.

A class of transition state analogue inhibitors of hGlxI are known which are S—(N-aryl/alkyl-N-hydroxycarbamoyl) glutathiones. Specifically, these thioester derivatives of GSH mimic the stereoelectronic features of the tightly bound transition state species that flank the ene-diolate intermediate that forms along the reaction coordinates of the enzyme. As such, these compounds are the strongest known competitive inhibitors of hGlxI, with inhibition constants ($K_i$s) in the mid-nanomolar range: S—(N-p-chlorophenyl-N-hydroxycarbamoyl)glutathione (CHG), $K_i$=46 nM; S—(N-p-bromophenyl-N-hydroxy-carbamoyl)glutathione (BHG), $K_i$=14 nM; S—(N-p-iodophenyl-N-hydroxy-carbamoyl)glutathione (IHG), $K_i$=10 nM; and S—(N-hexyl-N-hydroxycarbamoyl)glutathione, $K_i$=16 nM (Kalsi et al, *J. Med. Chem.*, 43:3981-3986 (2000)). These transition state analogue inhibitors are hereinafter called "reversible competitive inhibitors."

Moreover, the reversible competitive inhibitors are also slow substrates for bovine liver GlxII, which suggests that these compounds can selectively inhibit tumor cells over normal cells (Murthy et al, supra).

The effectiveness of the reversible competitive inhibitors can be measured by their specificity for the GlxI active site and by the time they occupy the active site, thereby blocking access of the enzyme's natural substrate (GSH-methylglyoxal thiohemiacetal). An inhibitor with a low competitive inhibition constant ($K_i$) associates with the active site of an enzyme with higher affinity and greater specificity, and therefore, occupies the active site for a longer period of time than inhibitors with higher $K_i$ values.

The competitive inhibitors have been shown to be lethal to different human and murine tumor cell lines in culture when administered as diethyl ester prodrugs (U.S. Pat. No. 5,616,563) (Kavarana et al, supra). Di- or mono-ester prodrugs are employed since the charged glutathionyl precludes rapid diffusion into cells. After diffusion, these prodrugs undergo de-esterification inside the cell. The diethyl ester prodrugs of S—(N-phenyl-N-hydroxycarbamoyl)glutathione, PHG(Et)$_2$; S—(N-p-bromophenyl-N-hydroxycarbamoyl)glutathione, BHG(Et)$_2$; and S—(N-p-chlorophenyl-N-hydroxycarbamoyl)glutathione, CHG(Et)$_2$, inhibit the growth of murine leukemia L1210 cells in culture with IC$_{50}$ values of 63, 16, and 5 µM, respectively, after 72 hours of incubation.

In vivo efficacy studies with CHG(Et)$_2$ by Sharkey et al, *Cancer Chemother. and Pharmacol.*, 46:156-166 (2000), which is herein incorporated by reference, also support the hypothesis that competitive inhibitors of GlxI are potentially important antitumor agents. For example, bolus i.v. administration of CHG(Et)$_2$ inhibited the growth of human prostate PC3 tumors in athymic nude mice. The potency of CGH (Et)$_2$ was as good as the positive control cisplatin without the cisplatin-associated haemopoetic toxicity. However, no effect was observed by continuous infusion of CHG(Et)$_2$ over 12 days, suggesting that, when administered by continuous infusion, not enough drug is available to be absorbed by such a rapidly growing tumor. Further, the efficacy of CHG(Et)$_2$ against murine melanotic melanoma implanted subcutaneously in (Es-1$^e$) mice was also evaluated. After, a preliminary pharmacokinetic study that showed significant accumulation of drug in melanoma following i.v. bolus administration of CHG(Et)$_2$, the efficacies of CHG(Et)$_2$ and the dicyclopentyl diester prodrug CHG(cyclopentyl)$_2$ were evaluated. All of the drugs gave results that were statistically significant from the vehicle control. CHG(Et)$_2$ and CHG(cyclopentyl)$_2$ were as effective as the positive control adriamycin, but at much higher dosages. There were no detectable side-effects observed in any of the trials. Similar results were obtained with athymic nude mice bearing human colon HT29 tumors. Potency was as good as the positive control vincristin when the drug was administered by continuous i.v. infusion, without any detectable side-effects. However, efficacy was not observed by bolus administration, indicating that this slowly growing tumor was not sufficiently exposed to drug. Thus, the method of drug delivery (bolus infusion versus continuous infusion) is an important aspect of efficacy.

All three in vivo efficacy studies required high doses of prodrug to inhibit tumor growth (80 mg/kg body mass). A subsequent series of studies by Sakamoto et al (2001) showed that the dicyclopentyl diester of a weaker competitive inhibitor of GlxI, (S-p-bromobenzyl)glutathione (BBG), effectively inhibited lung tumor cell lines NCI-H460, NCI-H226, A549, NCI-H23, DMS273, DMS114, NCI-H522 in vitro, and DMS144 and human prostate DU145 in nude mice bearing human cancer xenografts. Further, it was discovered that BBG is effective against human lung tumors (DMS114) in mice at dosages of 100 mg/kg (Sakamoto et al (2001), supra), with no evidence of adverse side effects during the 21 days of administration. Taken together, these studies show that inhibition of GlxI is an important chemotherapeutic strategy in cancer control.

In order to improve this antitumor strategy, more effective GlxI inhibitors must be developed that will be effective at much lower dosages. The large dosages currently required for antitumor activity increase the probability that toxic side effects or adverse reactions will develop when these compounds are used over long periods of time. Thus, there is a need in the art for more potent inhibitors that have a greater binding affinity or specificity for the active site of GlxI such that they may be administered at lower dosages than known GlxI inhibitors to effectively inhibit tumor growth.

SUMMARY OF THE INVENTION

An object of the present invention is to provide a class of molecules that will be stronger inhibitors of hGlxI activity. In one embodiment, this object has been met by bivalent GlxI inhibitors that simultaneously bind both active sites of the homodimeric enzyme having one active site per monomer. Such may be accomplished by tethering together S-substituted glutathiones or S-substituted glutathione prodrugs, via a chemical linker that allows simultaneous binding of each S-substituted glutathione or S-substituted glutathione prodrug to each active site of human GlxI. This results in a significant increase in net binding affinity of the bivalent inhibitor for the enzyme, as compared to a monovalent reversible competitive inhibitor, since the binding energies at each site contribute to the overall free energy of binding.

In another embodiment of the invention, the above object has been met by a class of monovalent inhibitors (herein called "irreversible inactivators") that irreversibly inactivate human GlxI by covalently modifying the active site.

Another object of the present invention is to provide an effective antitumor pharmaceutical composition with less adverse side effects than current chemotherapies. According to one embodiment of the invention, this object has been met by a bivalent GlxI inhibitor or a monovalent irreversible inactivator in combination with a pharmaceutically acceptable carrier.

A further object of the present invention is to provide a method of treating a subject having a neoplastic condition. According to one embodiment of the invention, this object has been met by a method comprising the step of administering to a subject having a neoplastic condition a pharmaceutically effective amount of a pharmaceutical composition comprising a bivalent inhibitor or a monovalent irreversible inactivator of human GlxI.

A still further object of the present invention is to provide a method of inhibiting the proliferation of a tumor cell. According to one embodiment of the invention this object has been met by a method comprising the step of contacting a tumor cell with an amount of a bivalent inhibitor of GlxI or a monovalent irreversible inactivator of GlxI that effectively inhibits proliferation of said tumor cell.

Other and further aspects, features, and advantages of the present invention will become apparent to a skilled artisan in view of the present disclosure of the invention as set forth herein.

DETAILED DESCRIPTION OF THE INVENTION

Figure 1:
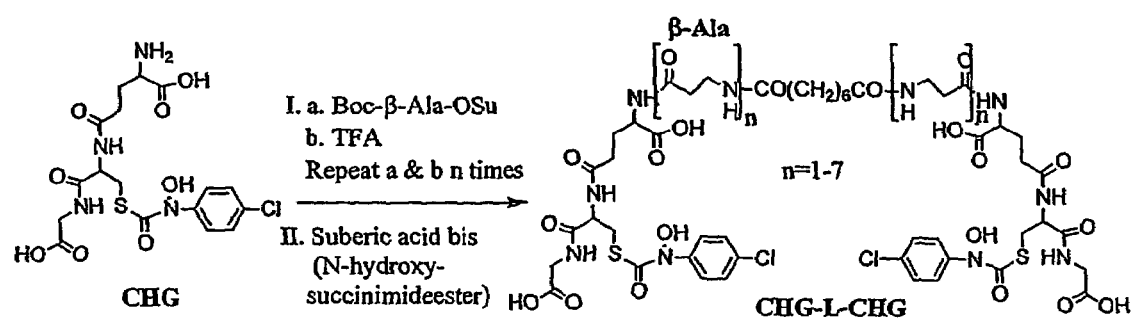
FIG. 1 shows a synthetic route to obtain bivalent transition state analogue inhibitors using poly-α-alanyl linkers.

The present invention provides compounds useful as antitumor agents comprising two human GlxI inhibitors covalently linked via a chemical linker, wherein each of said two human GlxI inhibitors, which may be the same or different, is an S-substituted glutathione or an S-substituted glutathione prodrug, wherein said GlxI inhibitors each have a γ-glutamyl amino group, wherein said chemical linker is covalently bound to each GlxI inhibitor via said γ-glutamyl amino group, and wherein said chemical linker has a length of at least 50 angstroms.

The human GlxI inhibitors are S-substituted glutathiones or corresponding prodrugs linked at the γ-glutamyl amino group. The X-ray crystal structure of the human GlxI in complex with one molecule of S—(N-p-chlorophenyl-N-hydroxycarbamoyl) glutathione (CHG) per active site shows that the γ-glutamyl amino groups of the bound CHGs are exposed to bulk solvent, and therefore cross-linking at the γ-glutamyl amino groups should not interfere with inhibitor binding. Further, the γ-glutamyl amino groups are about 30 to 40 Angstroms apart (Cameron et al, *Biochemistry,* 38:13480-13490 (1999)). The X-ray structure indicates that the [glycyl] carboxyl group of CHG might be another site of crosslinking, as this carboxyl group is at the solvent-protein interface in the x-ray structure of the hGlxI-CHG complex. However, the glycyl carboxyl group also appears to form a hydrogen bond with the enzyme. Indeed, ethylation of the glycyl carboxyl group leads to a 10-fold decrease in binding affinity (Murthy et al *J. Med. Chem.,* 37: 2161-2166 (1994). For this reason the glycyl carboxyl group is not an optimal site for crosslinking.

The particular S-substituted glutathione(s), S-substituted glutathione prodrug(s), or combination thereof, employed in the bivalent inhibitor is not critical, so long as the S-substituted glutathione is a human GlxI inhibitor. Numerous S-substituted glutathione GlxI inhibitors are known, such as, for example, the reversible competitive inhibitors including: S—(N-p-chlorophenyl-N-hydroxycarbamoyl)glutathione, S—(N-p-bromophenyl-N-hydroxycarbamoyl)glutathione, S—(N-p-iodophenyl-N-hydroxycarbamoyl)glutathione, S—(N-phenyl-N-hydroxycarbamoyl)glutathione, S-p-bromobenzyl-glutathione, and S—(N-alkyl-N-hydroxycarbamoyl)glutathione (where alkyl is methyl, ethyl, n-propyl, n-butyl, n-pentyl and n-hexyl. Particularly preferred are S—(N-aryl/alkyl-N-hydroxycarbamoyl)glutathiones.

Other S-substituted glutathiones or S-substituted glutathione prodrug(s) of the present invention include irreversible inactivators. Irreversible inactivators of the present invention are compounds of the formula S—(CH$_2$C(O)ORO C(O)CH$_2$X) glutathione, wherein R is selected from the group consisting of alkylene (C$_1$-C$_{20}$), (poly)ethylene glycol (CH$_2$CH$_2$O)$_{1-20}$, (poly)ethylene amine (CH$_2$CH$_2$N)$_{1-20}$, and arylene (C$_6$-C$_{20}$), and wherein X is a halogen. According to the invention, irreversible inactivators may be employed as monovalent GlxI inactivators, or alternatively, employed as bivalent inhibitors in combination with other irreversible inactivators or reversible competitive inhibitors.

Preferred irreversible inactivators are compounds of the formula CH$_2$C(O)O(CH$_2$)$_n$OC(O)CH$_2$X) glutathione, wherein n is 2 through 6 and wherein X is a halogen. Particularly preferred irreversible inactivators are S-(bromoacetoxy butyl acetoxy)glutathione and S-(bromoacetoxy propyl acetoxy)glutathione. Computational docking of these compounds into the X-ray crystal structure of hGlxI indicates that the S-substituents are ideally positioned to alkylate the sulfhydryl group of Cys60 in the active site, which is located about 12 to 13 Angstroms from the sulfur atom of the bound inactivators. Other irreversible inactivators are accommodated by the hGlxI active site, especially where the S-substituent is able to assume a "bowed" conformation in the active site, allowing the haloacetyl function to be positioned near Cys60.

Preferred irreversible inactivators have bromoacetoxy, chloroacetoxy, acryloyl and crotonyl groups. Particularly preferred are irreversible inactivators having a bromoacetoxy group.

U.S. Pat. No. 5,616,563, which is hereby incorporated by reference, describes methods of synthesis for S—(N-hydroxycarbamoyl)glutathione derivatives including: S—(N-p-chlorophenyl-N-hydroxycarbamoyl)glutathione, S—(N-p-bromophenyl-N-hydroxycarbamoyl)glutathione, S—(N-p-iodophenyl-N-hydroxycarbamoyl)glutathione, S—(N-phenyl-N-hydroxy-carbamoyl)glutathione. Moreover, the synthesis of the S—(N-aryl/alkyl-N-hydroxycarbamoyl)glutathiones is described by Kalsi, et al, *J. Med. Chem.* 2000, 43, 3981-3986.

According to the invention, any human GlxI inhibitor may be linked together to increase binding affinity for the enzyme over the monovalent form of the inhibitor. Particularly preferred, is the linking of a relatively high affinity reversible competitive inhibitor, such as CHG, to a lower affinity irreversible inactivator, such as S-(bromoacetoxy butyl acetoxy) glutathione and S-(bromoacetoxy propyl acetoxy)glutathione.

While any S-substituted glutathione may be employed according to the invention, one skilled in the art understands that the hydrophobicity of the S-substituent correlates with a higher affinity for the human GlxI active site (Kalsi 2000, supra). Moreover, the S—(N-aryl-N-hydroxycarbamoyl)-glutathione derivatives bind especially tightly to the active site of GlxI, as these compounds mimic the stereoelectronic features of the tightly bound transition state formed along the reaction coordinate of the enzyme during normal catalysis.

Other preferred embodiments employ human GlxI inhibitor(s), either monovalent GlxI inactivators or bivalent inhibitors/inactivators, that are catalytically hydrolyzed by human GlxII, a thioester hydrolase that is abundant in normal tissues, but deficient in tumor tissues. This is one possible basis for tumor targeting, since such compounds are believed herein to accumulate specifically in tumor cells. For example, S—(N-p-chlorophenyl-N-hydroxycarbamoyl)glutathione, S—(N-p-bromophenyl-N-hydroxycarbamoyl)glutathione, S—(N-phenyl-N-hydroxycarbamoyl)glutathione, and S—(N-methyl-N-hydroxycarbamoyl)glutathione are substrates for bovine liver GlxII. It is believed herein that incorporating these S-substituted glutathiones into bivalent inhibitors will not impact the ability of GlxII to hydrolyze the S-substituted glutathiones, based upon the X-ray structure of S—(N-p-bromophenyl-N-hydroxycarbamoyl)glutathione in complex with human GlxII, where the alpha amino group of the gamma-glutamyl residue of the inhibitor points into solvent (Cameron, et al., *Structure Fold Des* 1999, 7, 1067-1078). Therefore, covalent modification of the amino group, due to chemical crosslinking, is unlikely to affect binding of the S-substituted glutathione to the active site or the catalytic activity of the enzyme.

As used herein, the term "S-substituted glutathione prodrug" refers to any [glycyl, glutamyl] dialkyl, diaryl or diarylalkyl ester or [glycyl] or [glutamyl] mono-alkyl, mono-aryl or mono-arylalkyl esters of an S-substituted glutathione. Preferred embodiments include mono- or diethyl esters, mono- or di-n-propyl or mono- or diisopropyl esters, and mono- or di-cyclopentyl esters. The rates of cellular accumulation of the prodrugs described above are believed to increase with increasing hydrophobicity of the ester functions, as accumulation involves simple passive diffusion across the cell membrane (Kavarana et al J. Med. Chem. 42: 221-228 (1999))

The particular chemical linker employed in the bivalent GlxI inhibitor is not critical, so long as it is of a length to bridge the S-substituted glutathiones bound to the active sites of the dimeric human GlxI. It is preferred that the chemical linker be at least 50 Angstroms in length. More preferably, the chemical linker is at least 60 Angstroms in length. More preferably still, the chemical linker is at least 70 Angstroms in length.

The chemical nature of the linker is also not critical, so long as the linker does not interfere with binding of the multivalent inhibitor to the human GlxI active sites. Examples of suitable groups that may comprise the chemical linker include polyethylene glycol, poly-β-alanyl, alkyl, amide, and ester. Particularly preferred are chemical linkers comprising polyethylene glycol and poly-β-alanyl. More preferred is a chemical linker comprising $(\beta\text{-Ala})_{5-7}$.

Other preferred chemical linkers according to the present invention include chemical linkers represented by the formula:

$$(Z_1)_a-(Z_2)_b-(Z_3)_c$$

wherein $Z_1$, $Z_2$, and $Z_3$, which may be the same or different, are each selected from the group consisting of:
$C(O)(CH_2)_d NH$,
$CO(CH_2)_e C(O)$,
$(CH_2CH_2)_f NHC(O)$,
$(CH_2CH_2)_g—C(O)NH$,
$(CH_2)_h C(O) (OCH_2CH_2)_i NHC(O)(CH_2)_j C(O)$,
$NH(CH_2)_k (OCH_2CH_2)_l—O(CH_2) NH$,
$(CH_2)_n C(O)(OCH_2CH_2)_o NH(C(O)(CH_2)_p NH_q C(O)\text{-alkyl}$,
and
$C(O)NH(CH_2)_r NHC(O)—(CH_2)_s C(O)(NHCH_2CH_2)_t NH(C(O)(CH_2)_u NH)_v C(O)\text{-alkyl}$;

wherein subscripts a though v are independently 1-20.

In a preferred embodiment, the bivalent inhibitor of the present invention is represented by the formula:

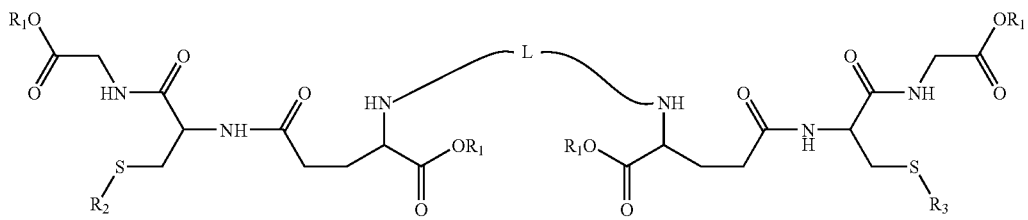

where L is a chemical linker represented by the formula $(Z_1)_a(Z_2)_b-(Z_3)_c$, wherein $Z_3$, $Z_2$ and $Z_3$, which may be the same or different, are each selected from the group consisting of:
$C(O)(CH_2)_dNH$,
$CO(CH_2)_eC(O)$,
$(CH_2CH_2)_fNHC(O)$,
$(CH_2CH_2)_g-C(O)NH$,
$(CH_2)_hC(O)(OCH_2CH_2)_iNHC(O)(CH_2)_jC(O)$,
$NH(CH_2)_k(OCH_2CH_2)_l-O(CH_2)_mNH$,
$(CH_2)_nC(O)(OCH_2CH_2)_oNH(C(O)(CH_2)_pNH)_qC(O)$-alkyl, and
$C(O)NH(CH_2)_rNHC(O)-(CH_2)_sC(O)(NHCH_2CH_2)_tNH(C(O)(CH_2)_uNH)_vC(O)$-alkyl;

wherein subscripts a through v are independently 1-20;

wherein $R_1$ is hydrogen or a member selected from the group consisting of:
(1) an alkyl($C_1$-$C_{18}$) optionally substituted with a halogen or arylalkyl ($C_6$-$C_{20}$)
(2) a cycloalkyl($C_3$-$C_8$) optionally substituted with a halogen, alkyl($C_1$-$C_{18}$) or arylalkyl($C_6$-$C_{20}$);
(3) a cycloalkenyl($C_5$-$C_7$) optionally substituted with a halogen, alkyl($C_1$-$C_{18}$) or arylalkyl($C_6$-$C_{20}$); and
(4) an aryl($C_6$-$C_{20}$) optionally substituted with a halogen, alkyl($C_1$-$C_{18}$) or arylalkyl ($C_6$-$C_{20}$);

wherein $R_2$ and $R_3$, which may be the same or different, are each selected from the group consisting of:
(1) an alkyl($C_1$-$C_{18}$) optionally substituted with a halogen or arylalkyl ($C_6$-$C_{20}$);
(2) a cycloalkyl($C_3$-$C_8$) optionally substituted with a halogen, alkyl($C_1$-$C_{18}$) or arylalkyl($C_6$-$C_{20}$);
(3) a cycloalkenyl($C_5$-$C_7$) optionally substituted with a halogen, alkyl($C_1$-$C_{18}$) or arylalkyl($C_6$-$C_{20}$); and
(4) an aryl($C_6$-$C_{20}$) optionally substituted with halogen, alkyl($C_1$-$C_{18}$), or arylalkyl ($C_6$-$C_{20}$).

Particularly preferred are compounds wherein $R_2$ and $R_3$, which may be the same or different, are each selected from the group consisting of:
(1) an alkyl($C_6$-$C_{10}$) optionally substituted with a halogen or arylalkyl($C_6$-$C_{10}$);
(2) a cycloalkyl($C_3$-$C_8$) optionally substituted with a halogen, alkyl($C_1$-$C_6$) or arylalkyl($C_6$-$C_{10}$);
(3) a cycloalkenyl($C_6$-$C_7$) optionally substituted with a halogen, alkyl($C_1$-$C_6$) or arylalkyl($C_6$-$C_{10}$), and
(4) an aryl($C_6$-$C_{12}$) optionally substituted with a halogen, alkyl($C_1$-$C_6$) or arylalkyl ($C_6$-$C_{10}$).

In another preferred embodiment, the bivalent inhibitor of the present invention is represented by the formula:

$C(O)(CH_2)_dNH$,
$CO(CH_2)_eC(O)$,
$(CH_2CH_2)_fNHC(O)$,
$(CH_2CH_2)_g-C(O)NH$,
$(CH_2)_hC(O)(OCH_2CH_2)_iNHC(O)(CH_2)_jC(O)$,
$NH(CH_2)_k(OCH_2CH_2)_l-O(CH_2)_mNH$,
$(CH_2)_nC(O)(OCH_2CH_2)_oNH(C(O)(CH_2)_pNH)_qC(O)$-alkyl,
and $C(O)NH(CH_2)_rNHC(O)-(CH_2)_sC(O)(NHCH_2CH_2)_tNH(C(O)(CH_2)_uNH)_vC(O)$-alkyl;

wherein subscripts a through v are independently 1-20;

wherein $R_1$ is hydrogen or a member selected from the group consisting of:
(1) an alkyl($C_1$-$C_{18}$) optionally substituted with a halogen or arylalkyl ($C_6$-$C_{20}$);
(2) a cycloalkyl($C_3$-$C_8$) optionally substituted with a halogen, alkyl($C_1$-$C_{18}$) or arylalkyl($C_6$-$C_{20}$);
(3) a cycloalkenyl($C_5$-$C_7$) optionally substituted with a halogen, alkyl($C_3$-$C_{18}$) or arylalkyl($C_6$-$C_{20}$); and
(4) an aryl($C_6$-$C_{20}$) optionally substituted with a halogen, alkyl($C_1$-$C_{18}$) or arylalkyl ($C_6$-$C_{20}$);

wherein $R_2$ and $R_3$, which may be the same or different, are each represented by a formula selected from the group consisting of:
—$R_6C(O)X(R_4)X_1C(O)Y$, wherein $R_6$ is alkylene ($C_1$-$C_6$) or arylene ($C_6$-$C_{20}$); X and $X_1$, which may be the same or different, are O, N, or C; $R_4$ is selected from the group consisting of alkylene ($C_1$-$C_{20}$), (poly)ethylene glycol $(CH_2CH_2O)_{1-20}$, (poly)ethylene amine $(CH_2CH_2N)_{1-20}$, and arylene ($C_6$-$C_{20}$); and Y is halomethylene or alkenyl($C_1$-$C_{20}$);
—$C(O)N(OH)X(R_4)X_1C(O)Y$, wherein X and $X_1$, which may be the same or different, are O, N, or C; $R_4$ is selected from the group consisting of alkylene ($C_1$-$C_{20}$), (poly)ethylene glycol $(CH_2CH_2O)_{1-20}$, (poly) ethylene amine $(CH_2CH_2N)_{1-20}$, and arylene ($C_6$-$C_{20}$); and Y is halomethylene or alkenyl($C_1$-$C_{20}$), and $C(O)X(R_4)X_1C(O)Y$, wherein X and $X_1$, which may be the same or different, are O, N, or C; $R_4$ is selected from the group consisting of alkylene ($C_1$-$C_{20}$), (poly)ethylene glycol $(CH_2CH_2O)_{1-20}$, (poly)ethylene amine $(CH_2CH_2N)_{1-20}$, and arylene ($C_6$-$C_{20}$); and Y is halomethylene or alkenyl($C_1$-$C_{20}$).

Particularly preferred are compounds wherein $R_1$ is hydrogen or a member selected from the group consisting of:
(1) an alkyl($C_1$-$C_8$) optionally substituted with a halogen or arylalkyl($C_6$-$C_{20}$);
(2) a cycloalkyl($C_3$-$C_8$) optionally substituted with a halogen, alkyl($C_1$-$C_{10}$) or arylalkyl($C_6$-$C_{20}$);
(3) a cycloalkenyl($C_5$-$C_7$) optionally substituted with a halogen, alkyl($C_1$-$C_{10}$) or arylalkyl($C_6$-$C_{20}$); and

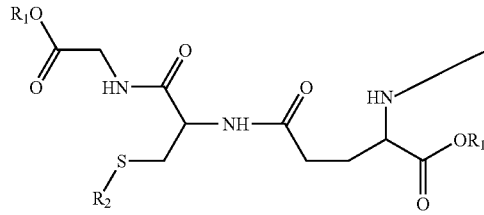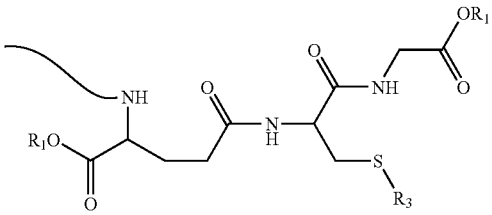

where L is a chemical linker represented by the formula $(Z_1)_a(Z_2)_b-(Z_3)_c$, wherein $Z_1$, $Z_2$ and $Z_3$, which may be the same or different, are each selected from the group consisting of:

(4) an aryl($C_6$-$C_{10}$) optionally substituted with a halogen, alkyl($C_1$-$C_{10}$), or arylalkyl($C_6$-$C_{20}$); and wherein $R_2$ and $R_3$, which may be the same or different, are each represented by a formula selected from the group consisting of:

—$R_6C(O)X(R_4)X_1C(O)Y$, wherein $R_6$ is alkylene ($C_3$-$C_6$) or arylene ($C_6$-$C_{12}$); X and $X_1$, which may be the same or different, are O, N, or C; $R_4$ is selected from the group consisting of alkylene ($C_1$-$C_{10}$), (poly)ethylene glycol $(CH_2CH_2O)_{1-10}$, (poly)ethylene amine $(CH_2CH_2N)_{1-10}$, and arylene ($C_6$-$C_{12}$); and Y is halomethylene or alkenyl($C_1$-$C_{10}$);

—$C(O)N(OH)X(R_4)X_1C(O)Y$, wherein X and $X_1$, which may be the same or different, are O, N, or C; $R_4$ is selected from the group consisting of alkylene ($C_3$-$C_{10}$), (poly)ethylene glycol $(CH_2CH_2O)_{1-10}$, (poly)ethylene amine $(CH_2CH_2N)_{1-10}$, and arylene ($C_6$-$C_{12}$); and Y is halomethylene or alkenyl($C_1$-$C_{10}$), and —$C(O)X(R_4)X_1C(O)Y$, wherein X and $X_1$, which may be the same or different are O, N, or C; $R_4$ is selected from the group consisting of alkylene ($C_3$-$C_{10}$), (poly)ethylene glycol $(CH_2CH_2O)_{1-10}$, (poly)ethylene amine $(CH_2CH_2N)_{1-10}$, and arylene ($C_6$-$C_{12}$); and Y is halomethylene or alkenyl($C_1$-$C_{10}$).

Other preferred bivalent inhibitors of the present invention include animal studies. For example, the fact that the bivalent reversible inhibitors bind about 100-fold more tightly to hGlxI relative to the corresponding monovalent reversible inhibitors, and the fact that the effective dose to produce inhibition of tumor growth using the monovalent reversible inhibitors in tumor-bearing mice is about 80 mg/kg every 12 h for two weeks (Sharkey et al 2000, supra), can be used to extrapolate a pharmaceutically effective dose for such inhibitors. Similar pharmaceutically effective amounts may be employed with the irreversible inactivators, but the dosing is less frequent. A preferred frequency is in the range of once every one to five days. The lower dosing frequency is predicated on the fact that the inactivators permanently destroy enzyme activity.

The compositions of, the invention may be administered to treat a neoplastic condition. Generally, the compositions of the present invention can be used to treat any cancerous condition. Preferred conditions are members selected from the group consisting of breast cancer, ovarian cancer, prostate cancer, lung cancer, colon cancer, kidney cancer, liver cancer,

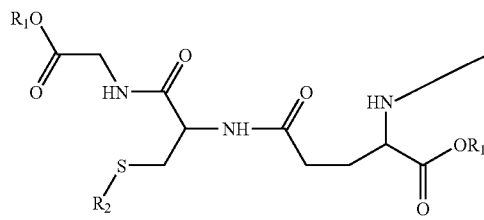
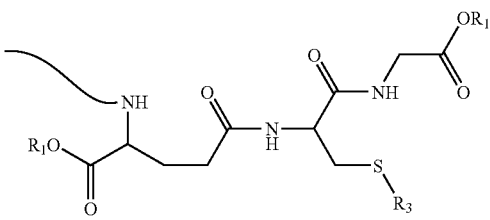

wherein $R_1$ is H or ethyl, wherein $R_2$ and $R_3$, which are the same, are —$C(O)N(OH)C_6H_4Cl$ or —$C(O)N(OH)C_6H_4Br$, and wherein L is —$(C(O)C_2H_4NH)_nC(O)C_6H_{12}C(O)(NHC_2H_4C(O))_n$—, wherein n is 6 or 7.

In one embodiment of the invention, the compound of the invention is in the form of a pharmaceutically acceptable salt or hydrate. Preferred salts include sodium and potassium salts.

The present invention further provides pharmaceutical compositions comprising a monovalent GlxI irreversible inactivators or bivalent GlxI inhibitors and a pharmaceutically acceptable carrier. While pharmaceutically acceptable carriers are known in the art, and are not critical to the invention, a preferred pharmaceutically acceptable carrier is aqueous isopropyl-β-cyclodextran, as the GlxI inhibitors described above are very soluble in this vehicle. Moreover, this vehicle prevents local, drug-dependent necrosis at the site of injection during i.v. delivery (Sharkey et al Cancer Chemother. and Pharmacol. 46: 156-166 (2000)).

The present invention further provides methods of treating a subject having a neoplastic condition comprising administering to a subject in need of such treatment a pharmaceutically effective amount of a composition comprising a monovalent irreversible inactivator or bivalent inhibitor of the invention.

The particular amount administered is not critical to the present invention, and varies depending on the age, weight, sex of the subject, the mode of administration, and the neoplastic condition being treated.

Typically, a pharmaceutically effective amount is a dose of from 0.001 mg/kg to about 5.0 mg/kg for the bivalent reversible inhibitors of hGlxI. A preferred dose is from 0.001 mg/kg to about 1 mg/kg. A pharmaceutically effective dose may also be extrapolated from in vitro binding data as well as from brain cancer, and haemopoetic tissue cancer. More preferred cancers are prostate, colon and lung tumors, which overexpress GlxI, as these tumors have previously been shown to be particularly sensitive to GlxI inhibition by competitive GlxI inhibitors (Sharkey et al 2000, supra; Sakamoto et al (2001), supra).

Although the compositions of the present invention may be administered in any favorable fashion, common routes include orally, intravenously, subcutaneously, or intramuscularly. In vivo efficacy studies with tumor-bearing mice indicates that intravenous administration (i.v.) is a preferred route.

The composition of the present invention may be administered by continuous i.v. infusion or bolus i.v. infusion to a subject having a neoplastic condition. In vivo efficacy studies with tumor-bearing mice suggests that slow growing tumors are preferably treated by continuous infusion, while rapidly growing tumors are preferably treated by i.v. bolus administration (Sharkey et al 2000, supra).

The present invention also provides methods of inhibiting the proliferation of a tumor cell comprising contacting a tumor cell with an amount of a composition of the invention effective to inhibit proliferation of said tumor cell. In a preferred embodiment, an effective amount to inhibit proliferation of a tumor cell in vivo is in a range of 0.1 to about 5 mg/kg/12 h of a bivalent inhibitor or a monovalent irreversible inactivator. In another preferred embodiment, an effective amount to inhibit proliferation of a tumor cell in vitro with a bivalent inhibitor is a concentration in a range of 1-100 nM, and preferably less than 50 nM. An effective amount to inhibit proliferation of a tumor cell in vitro with a monovalent irreversible inactivator is a concentration of less than 200 nM, and preferably less than 100 nM.

The following examples are given for the purpose of illustrating various embodiments of the invention and are not meant to limit the present invention in any fashion.

Example 1

Synthesis of Irreversible Inactivators

Figure 6:
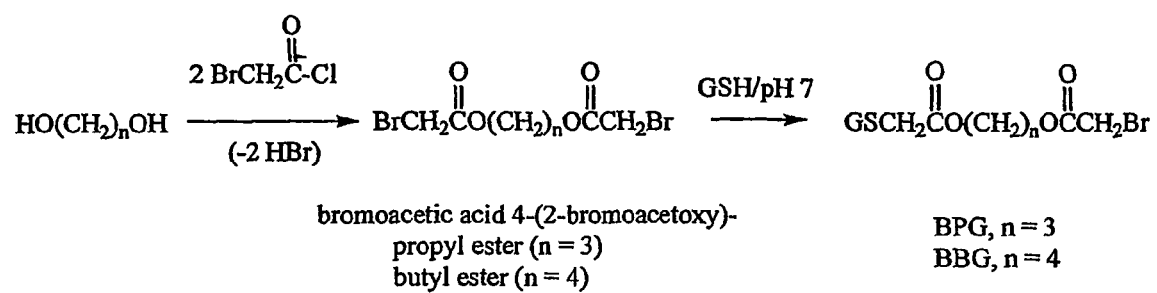
FIG. 6 shows a synthetic route for the irreversible inactivators S-(bromoacetoxy butyl acetoxy)glutathione (BBG) and S-(bromoacetoxy propyl acetoxy)glutathione (BPG).

The synthetic route used to prepare the irreversible inactivators of hGlxI, S-(bromoacetoxy propyl acetoxy)glutathione (BPG) and S-(bromoacetoxy butyl acetoxy)glutathione (BBG), is shown in FIG. 6.

Bromoacetic Acid 3-(2-Bromoacetoxy) Propyl Ester

To a 100 ml round-bottom flask, equipped with a drying tube, was added 50 ml methylene chloride, bromoacetyl chloride (1.03 g, 26 mmol) and 1,3-propanediol (13 mmol). The mixture was refluxed under nitrogen and the reaction followed to completion (~48 h), on the basis of the disappearance of bromoacetyl chloride on silica gel TLC (chloroform:methanol 95:5 v/v), Rf=0.5, and the appearance of a product spot at Rf=0.90. The solvent was removed in vacuo to give the crude product as a light brown oil. Yield: 84%. $^1$H NMR 300 MHz (CDCl$_3$, TMS) δ 3.85 (4H, s, —C(O)CH$_2$Br), 4.29 (4H, t, J=6.23 Hz, —OCH$_2$CH$_2$—), 2.07 (2H, p, J=6.23 Hz, —OCH$_2$CH$_2$—). Anal. (C$_7$H$_{10}$O$_2$Br$_2$): C calcd 26.59. found 27.74; H calcd 3.19 found 3.46.

Bromoacetic Acid 4-(2-Bromoacetoxy) Butyl Ester

This compound was prepared by a procedure analogous to that used for the preparation of bromoacetic acid 3-(2-bromoacetoxy)propyl ester. The mixture was refluxed under nitrogen and the reaction followed to completion (~48 h), on the basis of the disappearance of bromoacetyl chloride on silica gel TLC (chloroform:methanol 90:10 v/v), Rf=0.39, and the appearance of a product spot at Rf=0.78. The solvent was removed in vacuo to give the crude product as yellow crystals: mp 62-62.5° C. Yield: ~80%. $^1$H NMR 300 MHz (CDCl$_3$, TMS) δ 3.84 (4H, s, —C(O)CH$_2$Br), 1.78 (4H, p, J ~3 Hz, —OCH$_2$CH$_2$—). 4.22 (4H, t, J ~3 Hz, —OCH$_2$CH$_2$—), Anal. (C$_9$H$_{14}$O$_2$Br$_2$) C calcd 28.94. found 29.33; H calcd 3.64. found 3.46.

S-(Bromoacetoxy propyl acetoxy)glutathione (BPG)

To a solution of bromoacetic acid 3-(2-bromoacetoxy)propyl ester (1.05 g, 3.29 mmol) in 18 ml of acetone was slowly added an aqueous, out-gassed solution of GSH (0.2 g, 0.65° mmol) in 10 ml H$_2$O containing 1 molar equivalent of NaOH. The mixture was allowed to stir at room temperature for 3 h. The mixture was washed with CHCl$_3$ (4×60 ml). Aqueous layer was decanted from the organic layer and the solvent was removed from the aqueous layer in vacuo. The glassy residue was purified by reverse-phase HPLC (Waters μBondapak C$_{18}$, 7.8×300 mm) using a running solvent composed of H$_2$O:MeOH:acetic acid (80:20:1, v/v/v). Yield: 18%. $^1$H NMR 300 MHz (D$_2$O, ref HOD (δ 4.8)) δ 3.931 (2H, s, —C(O)CH$_2$Br), 2.045 (2H, p, J=6.4 Hz —OCH$_2$CH$_2$—), 4.247 (2H, t, J=3.9 Hz, —SCH$_2$C(O)OCH$_2$CH$_2$—), 4.227 (2H, t, J=3.9 Hz, BrCH$_2$C(O)OCH$_2$CH$_2$—), 4.015 (2H, s, Gly-CH$_2$), 3.412 (2H, s, —SCH$_2$C(O)O), 2.920 (1H, q, J=14.7, 9.0 Hz, —CCH$_x$H$_y$S—), 3.122 (1H, q, J=14.7, 5.2 Hz, —CCH$_x$H$_y$S—), 4.581 (1H, q, J=14.1, 6.0 Hz, Cys-CH), 2.136 (2H, t, J=7.2, 7.2 Hz, -Glu-C$_\beta$H$_2$), 2.511 (2H, t, J=7.2, 7.2 Hz, -Glu-C$_\gamma$H$_2$), 3.775 (1H, t, J=6.0, 6.0 Hz, -Glu-C$_\alpha$H).

S-(Bromoacetoxy butyl acetoxy)glutathione (BBG)

This compound was synthesized by the same general procedure used to synthesize BPG. Yield: 17%. $^1$H NMR 300 MHz (D$_2$O, ref HOD (δ 4.8)) δ 3.926 (2H, s, —C(O)CH$_2$Br), 1.752 (4H, m, —OCH$_2$CH$_2$—), 4.191 (2H, t, J=3.9 Hz, —SCH$_2$C(O)OCH$_2$CH$_2$—), 4.216 (2H, t, J=3.9 Hz, BrCH$_2$C(O)OCH$_2$CH$_2$—), 4.015 (2H, s, Gly-CH$_2$), 3.412 (2H, s, —SCH$_2$C(O)O), 2.920 (1H, q, J=14.7, 9.0 Hz, —CCH$_x$H$_y$S—), 3.122 (1H, q, J=14.7, 5.2 Hz, —CCH$_x$H$_y$S—), 4.581 (1H, q, J=14.1, 6.0 Hz, Cys-CH), 2.136 (2H, t, J=7.2, 7.2 Hz, -Glu-C$_\beta$H$_2$), 2.511 (2H, t, J=7.2, 7.2 Hz, -Glu-C$_\gamma$H$_2$), 3.775 (1H, t, J=6.0, 6.0 Hz, -Glu-C$_\alpha$H). ESI MS: (M (Br$_{79}$)+H$^+$), 558.53, (M (Br$_{81}$)+H$^+$), 560.53.

Example 2

Irreversible Inactivation of Human GlxI

The invention provides a class of S-substituted glutathiones that irreversibly inactivate hGlxI. Irreversible inactivators of GlxI bind to the active site and permanently disable the enzyme via covalent modification. Irreversible inactivators with high affinity (low dissociation constant, K$_d$) are preferred over prior art compounds because the effect of GlxI inhibition is usually longer lasting.

Inactivation Kinetics

Figure 7:
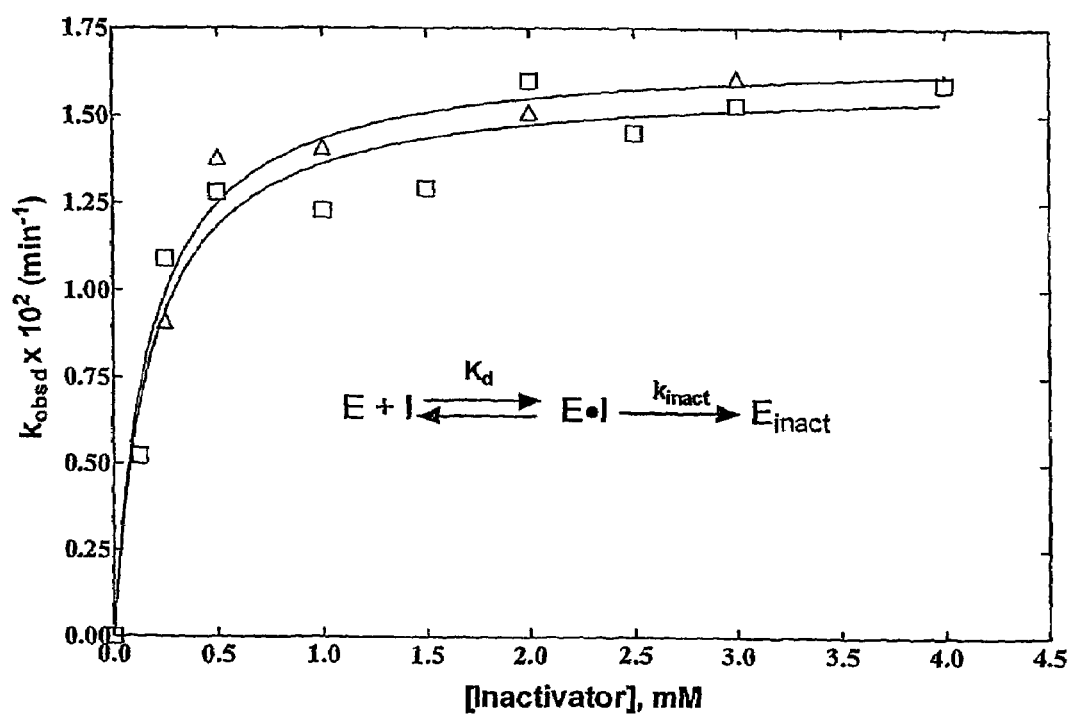
FIG. 7 shows first order rate constants ($k_{obsd}$) for inactivation of human GlxI versus concentration of GSCH$_2$C(O)O(CH$_2$)$_4$OC(O)CH$_2$Br ($K_d$=177±43 µM, $k_{inact}$=0.0160±0.0007 min$^{-1}$). Values of $K_d$ and $k_{inact}$ were obtained by fitting the data to: $k_{obsd}=k_{inact}[\text{inact}]/(K_d+[\text{inact}])$.

As shown in FIG. 7, both S-(Bromoacetoxy propyl acetoxy)glutathione (BPG) and S-(bromoacetoxy butyl acetoxy)glutathione (BBG) irreversibly inactivate human GlxI (Conditions: Glycerol (20%) in aqueous sodium phosphate buffer, pH 7, 25° C.). Incubation mixtures of enzyme (10 units/ml) and known concentrations of inactivator in phosphate buffer were separately incubated in plastic bullet tubes maintained at 25° C. in a water bath. Aliquots were removed, diluted into a quartz cuvette containing one ml GSH-methylglyoxal-thiohemiacetal, and the rate of product formation (ΔOD (240)) monitored as a function of time. From the initial rate of product formation, the activity of the enzyme was calculated. The slope of a plot of ln (fraction of enzyme activity remaining) versus time gives the apparent first-order rate constant (k$_{inact}$) for inactivation of hGlxI. A plot of k$_{inact}$ versus inactivator concentration (FIG. 7.) gives the dissociation constant (K$_d$ and the maximum value of k$_{inact}$).

Both compounds likely inactivate the enzyme by covalently modifying an active site base, as the reversible inhibitor CHG protects the enzyme from inactivation, and the inactivation process exhibits saturation kinetics (FIG. 7). Moreover, matrix assisted laser desorption (MALDI) mass spectrometry of the inactivated enzyme indicates that the polypeptide composing each monomer has been covalently modified by a single inactivator molecule, with the loss of a bromine atom from the inactivator. Computational docking of BPG and BBG into the active site of hGlxI, suggests that the sulfhydryl group of Cys (60) is well positioned to react with bound BBG and bound BPG (displacing Br$^-$) during inactivation of the enzyme.

Example 3

Synthesis of Bivalent GlxI Inhibitors Containing Poly-β-alanyl Linkers

The synthetic route used to generate bivalent competitive inhibitors of GlxI by cross-linking the reversible competitive inhibitor S-(4-chlorophenyl-N-hydroxyphenyl)glutathione (CHG) using poly-β-alanyl linkers is shown in FIG. 1.

Materials and Methods

Oxidized and reduced glutathione, suberic acid bis(N-hydroxysuccinimide ester), human and yeast glyoxalase I, bovine liver glyoxalase II, human placenta glutathione transferase and yeast glutathione reductase were purchased from Sigma Chem. Co. Boc-β-Ala-OSu was purchased from Novabiochem. All other reagents were of the highest purity commercially available.

Analytical Methods

NMR spectra were taken on a GE QE-500 NMR spectrometer. Mass spectral data were obtained at the Center for Biomedical and Bio-organic Mass Spectrometry, Washington University. UV spectra were recorded using a Beckman DU 640 spectrophotometer. HPLC was carried out using a Waters high-performance liquid chromatography system composed of a 600 Controller, Delta 600 Pumps, and 996 Photodiode Array Detector. Analytical HPLC was performed using a Nova-Pak $C_{18}$, 4 μm, 3.9×150 mm column. Preparative HPLC was performed using a SymmetryPrep $C_{18}$, 7 μm, 19×150 mm column.

CHG(β-ala)

To a solution of CHG (1 g, 2.1 mmol) in a mixture of 15 ml of DMF and 3 ml of diisopropylethylamine was added Boc-β-Ala-OSu (900 mg, 3.6 mmol). The reaction mixture was stirred at room temperature and the progress of the reaction was monitored by following the disappearance of the CHG peak obtained by RP-HPLC of aliquots of the reaction mixture, using 25% acetonitrile in water containing 0.1% trifluoroacetic acid as an eluting solvent. After the reaction had gone to 99% completion (~1.5 h), solvent was removed in vacuo, the residue dissolved in 10 ml TFA and stirred for 1 h at room temperature. Diethyl ether (100 ml) was added to the reaction mixture and the precipitate was collected by filtration. The crude product was fractionated by reverse-phase HPLC (Waters Symmetry prep $C_{18}$, 7 μm, 19×150 mm) using the same running solvent. The product peaks were collected, evaporated to dryness and maintained under vacuum overnight to give the final product as a white solid: yield 89% (1.15 g) $^1$H NMR (500 MHz, $D_2O$ TRIS buffer, pD 8.7) δ 7.49 (d, J=8.9 Hz, 2H), 7.44 (d, J=8.9 Hz, 2H), 4.60 (dd, J=8.8, 4.4 Hz, 1H), 4.14 (dd, J=8.8, 4.6 Hz, 1H), 3.78 (d, J=17.3 Hz, 1H), 3.74 (d, J=17.3 Hz, 1H), 3.35 (dd, J=14.5, 4.5 Hz, 1H), 3.21 (m, 2H), 3.12 (dd, J=14.5, 8.8 Hz, 1H), 2.65 (m, 2H), 2.38 (m, 2H), 2.11 (m, 1H), 1.94 (m, 1H). HRMS (ESI) m/z 548.1216 [M+H]$^+$ (calc'd for $C_{20}H_{27}N_5O_9SCl$: 548.1218).

CHG(β-ala)$_2$ through CHG(β-ala)$_7$

These compounds were prepared by the successive addition of Boc-β-Ala-OSu to CHG(β-ala) using the procedure described above: CHG(β-ala)$_2$. Yield: 75% (0.88 g). $^1$H NMR (500 MHz, $D_2O$ Tris buffer, pD 8.7) δ 7.48 (d, J=8.8 Hz, 2H), 7.44 (d, J=8.8 Hz, 2H), 4.62 (dd, J=8.8, 4.4 Hz, 1H), 4.15 (dd, J=8.4, 4.6 Hz, 1H), 3.77 (d, J=17.3 Hz, 1H), 3.74 (d, J=17.3 Hz, 1H), 3.41 (t, J=6.2 Hz, 2H), 3.37 (dd, J=14.5, 4.5 Hz, 1H), 3.19 (t, J=6.7 Hz, 2H), 3.12 (dd, J=14.5, 8.9 Hz, 1H), 2.60 (t, J=6.7 Hz, 2H), 2.44 (t, J=6.2 Hz, 2H), 2.36 (m, 2H), 2.10 (m, 1H), 1.93 (m, 1H). HRMS (ESI) m/z 619.1579 [M+H]$^+$ (calc'd for $C_{23}H_{32}N_6O_{10}SCl$: 619.1589); CHG(β-ala)$_3$. Yield: 75% (0.88 g). $^1$H NMR (500 MHz, $D_2O$ TRIS buffer, pD 8.7) δ 7.49 (d, J=8.9 Hz, 2H), 7.44 (d, J=8.9 Hz, 2H), 4.61 (dd, J=8.8, 4.4 Hz, 1H), 4.14 (dd, J=8.5, 4.8 Hz, 1H), 3.78 (d, J=17.1 Hz, 1H), 3.75 (d, J=17.1 Hz, 1H), 3.40 (m, 4H), 3.33 (dd, J=14.5, 4.6 Hz, 1H), 3.18 (t, J=6.7 Hz, 2H), 3.11 (dd, J=14.6, 8.9 Hz, 1H), 2.59 (t, J=6.7 Hz, 2H), 2.44 (t, J=6.2 Hz, 2H), 2.39 (t, J=6.6 Hz, 2H), 2.35 (m, 2H), 2.10 (m, 1H), 1.93 (m, 1H). HRMS (ESI) m/z 690.1944 [M+H]$^+$ (calc'd for $C_{26}H_{37}N_7O_{11}SCl$: 690.1960); CHG(β-ala)$_4$. Yield: 54% (0.37 g). $^1$H NMR (500 MHz, $D_2O$ TRIS buffer, pD 8.7) δ 7.49 (d, J=8.9 Hz, 2H), 7.44 (d, J=8.9 Hz, 2H), 4.61 (dd, J=8.6, 4.4 Hz, 1H), 4.15 (dd, J=8.1, 4.6 Hz, 1H), 3.78 (d, J=17.2 Hz, 1H), 3.75 (d, J=17.2 Hz, 1H), 3.41 (m, 6H), 3.35 (dd, J=14.4, 4.4 Hz, 1H), 3.19 (t, J=6.7 Hz, 2H), 3.11 (dd, J=14.6, 8.9 Hz, 1H), 2.58 (t, J=6.7 Hz, 2H), 2.45 (t, J=6.2 Hz, 2H), 2.40 (t, J=6.6 Hz, 2H), 2.10 (m, 1H), 1.93 (m, 1H). HRMS (ESI) m/z 761.2321 [M+H]$^+$ (calc'd for $C_{29}H_{42}N_8O_{12}SCl$: 761.2331); CHG(β-ala)$_5$. Yield: 50% (0.2 g). $^1$H NMR (500 MHz, $D_2O$ TRIS buffer, pD 8.7) δ 7.49 (d, J=8.9 Hz, 2H), 7.44 (d, J=8.9 Hz, 2H), 4.60 (dd, J=8.8, 4.4 Hz, 1H), 4.15 (dd, J=8.5, 4.8 Hz, 1H), 3.78 (d, J=17.2 Hz, 1H), 3.75 (d, J=17.2 Hz, 1H), 3.39 (m, 8H), 3.35 (dd, J=14.6, 4.4 Hz, 1H), 3.17 (t, J=6.7 Hz, 2H), 3.13 (dd, J=14.4, 8.9 Hz, 1H), 2.59 (t, J=6.7 Hz, 2H), 2.45 (t, J=6.4 Hz, 2H), 2.39 (m, 6H), 2.35 (m, 2H), 2.10 (m, 1H), 1.93 (m, 1H). HRMS (ESI) m/z 832.2715 [M+H]$^+$ (calc'd for $C_{32}H_{47}N_9O_{13}SCl$: 832.2703); CHG(β-ala)$_6$. Yield: 55% (0.12 g). $^1$H NMR (500 MHz, $D_2O$ TRIS buffer, pD 8.7) δ 7.49 (d, J=8.9 Hz, 2H), 7.44 (d, J=8.9 Hz, 2H), 4.59 (dd, J=8.8, 4.4 Hz, 1H), 4.15 (dd, J=8.5, 4.8 Hz, 1H), 3.78 (d, J=17.2 Hz, 1H), 3.75 (d, J=17.2 Hz, 1H), 3.41 (m, 10H), 3.30 (dd, J=14.5, 4.6 Hz, 1H), 3.10 (t, J=6.6 Hz, 2H), 2.95 (dd, J=14.4, 8.9 Hz, 1H), 2.55 (t, J=6.7 Hz, 2H), 2.41 (m, 8H), 2.35 (m, 2H), 2.10 (m, 1H), 1.93 (m, 1H). HRMS (ESI) m/z 903.3074 [M+H]$^+$ (calc'd for $C_{35}H_{52}N_{10}O_{14}SCl$: 903.3074); CHG(β-ala)$_7$. Yield: 55% (0.12 g). $^1$H NMR (500 MHz, $D_2O$ TRIS buffer, pD 8.7) δ 7.49 (d, J=8.9 Hz, 2H), 7.43 (d, J=8.9 Hz, 2H), 4.59 (dd, J=8.7, 4.4 Hz, 1H), 4.15 (dd, J=8.2, 4.6 Hz, 1H), 3.78 (d, J=17.4 Hz, 1H), 3.75 (d, J=17.4 Hz, 1H), 3.39 (m, 12H), 3.34 (dd, J=14.6, 4.5 Hz, 1H), 3.13 (t, J=6.5 Hz, 2H), 3.11 (dd, J=14.4, 8.9 Hz, 1H), 2.56 (t, J=6.7 Hz, 2H), 2.44 (t, J=6.5 Hz, 2H), 2.40 (m, 10H), 2.35 (m, 2H), 2.10 (m, 1H), 1.93 (m, 1H). HRMS (ESI) m/z 974.3434 [M+H]$^+$ (calc'd for $C_{38}H_{57}N_{11}O_{15}SCl$: 974.3445).

[CHG(β-ala)]$_2$Suberate Diamide

To a solution of CHG(β-ala) (14 mg, 0.026 mmol) in a mixture of 0.3 ml DMF and 0.1 ml diisopropylethylamine was added suberic acid bis(N-hydroxysuccinimideester) (4.7 mg, 0.013 mmol). The reaction mixture was stirring at room, temperature overnight. The solvent was removed in vacuo and the crude product was fractionated by preparative reverse-phase HPLC using a linear gradient of 25-40% acetonitrile in water containing 0.1% trifluoroacetic acid. The product peaks were collected, evaporated to dryness and maintained under vacuum overnight to give the final product as a white solid: yield 25% (4.1 mg). $^1$H NMR (500 MHz, $D_2O$ TRIS buffer, pD 8.7) δ 7.47 (d, J=8.8 Hz, 4H), 7.41 (d, J=8.8 Hz, 4H), 4.60 (dd, J=8.8, 4.3 Hz, 2H), 4.16 (dd, J=8.1, 4.7 Hz, 2H), 3.77 (d, J=17.2 Hz, 2H), 3.75 (d, J=17.2 Hz, 2H), 3.37 (m, 4H), 3.35 (dd, J=14.5, 4.2 Hz, 2H), 3.10 (dd, J=14.5, 9.0 Hz, 2H), 2.43 (m, 4H), 2.34 (m, 4H), 2.15 (t, J=7.4 Hz, 4H), 2.10 (m, 2H), 1.93 (m, 2H), 1.49 (m, 4H), 1.22 (m, 4H). HRMS (ESI) m/z 1255.2902 [M+Na]$^+$ (calc'd for $C_{48}H_{62}N_{10}O_{20}S_2Cl_2Na$: 1255.2858).

[CHG(β-ala)$_2$]$_2$Suberate Diamide Through [CHG(β-ala)$_7$]$_2$Suberate Diamide These compounds were prepared by crosslinking CHG(β-ala)$_2$-CHG(β-ala)$_7$ using the procedure described above for the preparation of [CHG(β-ala)]$_2$suberate diamide: [CHG(β-ala)$_2$]$_2$suberate diamide. $^1$H NMR (500 MHz, $D_2O$ TRIS buffer, pD 8.7) δ 7.48 (d, J=8.8 Hz, 4H), 7.41 (d, J=8.8 Hz, 4H), 4.61 (dd, J=8.7, 4.4 Hz, 2H), 4.16 (dd, J=8.2, 4.7 Hz, 2H), 3.77 (d, J=17.1 Hz, 2H), 3.75 (d, J=17.1 Hz, 2H), 3.38 (m, 8H), 3.34 (dd, J=14.5, 4.3 Hz, 2H), 3.11 (dd, J=14.5, 8.9 Hz, 2H), 2.43 (t, J=6.6 Hz, 4H), 2.38 (t, J=6.6 Hz, 4H), 2.34

(m, 4H), 2.16 (t, J=7.4 Hz, 4H), 2.10 (m, 2H), 1.93 (m, 2H), 1.50 (m, 4H), 1.23 (m, 4H). HRMS (ESI) m/z 1397.3572 [M+Na]$^+$ (calc'd for $C_{54}H_{72}N_{12}O_{22}S_2Cl_2$: 1397.3600); [CHG(β-ala)$_3$]$_2$suberate diamide. Yield 29% $^1$H NMR (500 MHz, D$_2$O TRIS buffer, pD 8.7) δ 7.49 (d, J=8.8 Hz, 4H), 7.42 (d, J=8.8 Hz, 4H), 4.60 (dd, J=8.8, 4.5 Hz, 2H), 4.15 (dd, J=8.2, 4.6 Hz, 2H), 3.77 (d, J=17.4 Hz, 2H), 3.75 (d, J=17.4 Hz, 2H), 3.38 (m, 12H), 3.34 (dd, J=14.5, 4.6 Hz, 2H), 3.11 (dd, J=14.6, 9.0 Hz, 2H), 2.39 (m, 12H), 2.34 (m, 4H), 2.17 (t, J=7.2 Hz, 4H), 2.10 (m, 2H), 1.93 (m, 2H), 1.50 (m, 4H), 1.24 (m, 4H). HRMS (ESI) m/z 759.2294 [M+2H]$^{2+}$ (calc'd for $C_{60}H_{84}N_{14}O_{24}S_2Cl_2$: 759.230); [CHG (β-ala)$_4$]$_2$suberate diamide. Yield 14% 1H NMR (500 MHz, D$_2$O TRIS buffer, pD 8.7) δ 7.44 (d, J=8.5 Hz, 4H), 7.37 (d, J=8.5 Hz, 4H), 4.54 (dd, J=8.7, 4.4 Hz, 2H), 4.10 (dd, J=8.2, 4.8 Hz, 2H), 3.73 (d, J=17.3 Hz, 2H), 3.71 (d, J=17.3 Hz, 2H), 3.34 (m, 16H), 3.29 (dd, J=14.5, 4.6 Hz, 2H), 3.06 (dd, J=14.5, 8.9 Hz, 2H), 2.33 (m, 16H), 2.30 (m, 4H), 2.13 (t, J=7.2 Hz, 4H), 2.10 (m, 2H), 1.90 (m, 2H), 1.49 (m, 4H), 1.20 (m, 4H). HRMS (ESI) m/z 852.2449 [M+2Na]$^{2+}$ (calc'd for $C_{66}H_{92}N_{16}O_{26}S_2Cl_2Na_2$: 852.249); [CHG (β-ala)$_5$]$_2$suberate diamide. Yield 18% $^1$H NMR (500 MHz, D$_2$O TRIS buffer, pD 8.7) δ 7.49 (d, J=8.4 Hz, 4H), 7.42 (d, J=8.4 Hz, 4H), 4.59 (dd, J=8.8, 4.4 Hz, 2H), 4.15 (dd, J=8.3, 4.8 Hz, 2H), 3.78 (d, J=17.3 Hz, 2H), 3.75 (d, J=17.3 Hz, 2H), 3.39 (m, 20H), 3.33 (dd, J=14.5, 4.4 Hz, 2H), 3.11 (dd, J=14.6, 8.9 Hz, 2H), 2.38 (m, 20H), 2.34 (m, 4H), 2.18 (t, J=7.3 Hz, 4H), 2.10 (m, 2H), 1.93 (m, 2H), 1.52 (m, 4H), 1.24 (m, 4H). HRMS (ESI) m/z 912.2955 [M+H+ Na]$^{2+}$ (calc'd for $C_{72}H_{103}N_{18}O_{28}S_2Cl_2Na$: 912.295); [CHG (β-ala)$_6$]$_2$suberate diamide. Yield 10% $^1$H NMR (500 MHz, D$_2$O TRIS buffer, pD 8.7)) δ 7.50 (d, J=8.7 Hz, 4H), 7.42 (d, J=8.7 Hz, 4H), 4.61 (dd, J=8.7, 4.4 Hz, 2H), 4.16 (dd, J=8.3, 4.7 Hz, 2H), 3.77 (d, J=17.1 Hz, 2H), 3.75 (d, J=17.1 Hz, 2H), 3.39 (m, 24H), 3.35 (dd, J=14.5, 4.5 Hz, 2H), 3.11 (dd, J=14.5, 8.9 Hz, 2H), 2.40 (m, 24H), 2.36 (m, 4H), 2.18 (t, J=7.3 Hz, 4H), 2.11 (m, 2H), 1.93 (m, 2H), 1.52 (m, 4H), 1.24 (m, 4H). HRMS (ESI) m/z 912.2955 [M+H+ Na]$^{2+}$ (calc'd for $C_{78}H_{113}N_{20}O_{30}S_2Cl_2Na$: 912.295); [CHG (β-ala)$_7$]$_2$suberate diamide. Yield 19% $^1$H NMR (500 MHz, D$_2$O TRIS buffer, pD 8.7) δ 7.49 (d, J=8.7 Hz, 4H), 7.42 (d, J=8.7 Hz, 4H), 4.59 (dd, J=8.8, 4.4 Hz, 2H), 4.15 (dd, J=8.2, 4.6 Hz, 2H), 3.78 (d, J=17.2 Hz, 2H), 3.75 (d, J=17.2 Hz, 2H), 3.39 (m, 28H), 3.33 (dd, J=14.4, 4.4 Hz, 2H), 3.11 (dd, J=14.4, 8.9 Hz, 2H), 2.40 (m, 28H), 2.34 (m, 4H), 2.18 (t, J=7.3 Hz, 4H), 2.09 (m, 2H), 1.93 (m, 2H), 1.53 (m, 4H), 1.24 (m, 4H). A good quality MS of this compound could not be obtained. However, a high quality HRMS (ESI) of the [glycyl, glutamyl] tetra-O-ethyl ester of this compound (m/z 1099.9457 [M+2H]$^{2+}$ (calc'd for $C_{92}H_{140}N_{22}O_{32}S_2Cl_2$: 1099.9420) indirectly confirmed the identity of [CHG(β-ala)$_7$]$_2$suberate diamide. The tetra O-ethyl ester was prepared by incubating [CHG(β-ala)$_7$]$_2$suberate diamide in ethanolic HCl.

Example 4

Synthesis of Bivalent Inhibitors Containing Polyethyleneglycol Linkers

Figure 2:
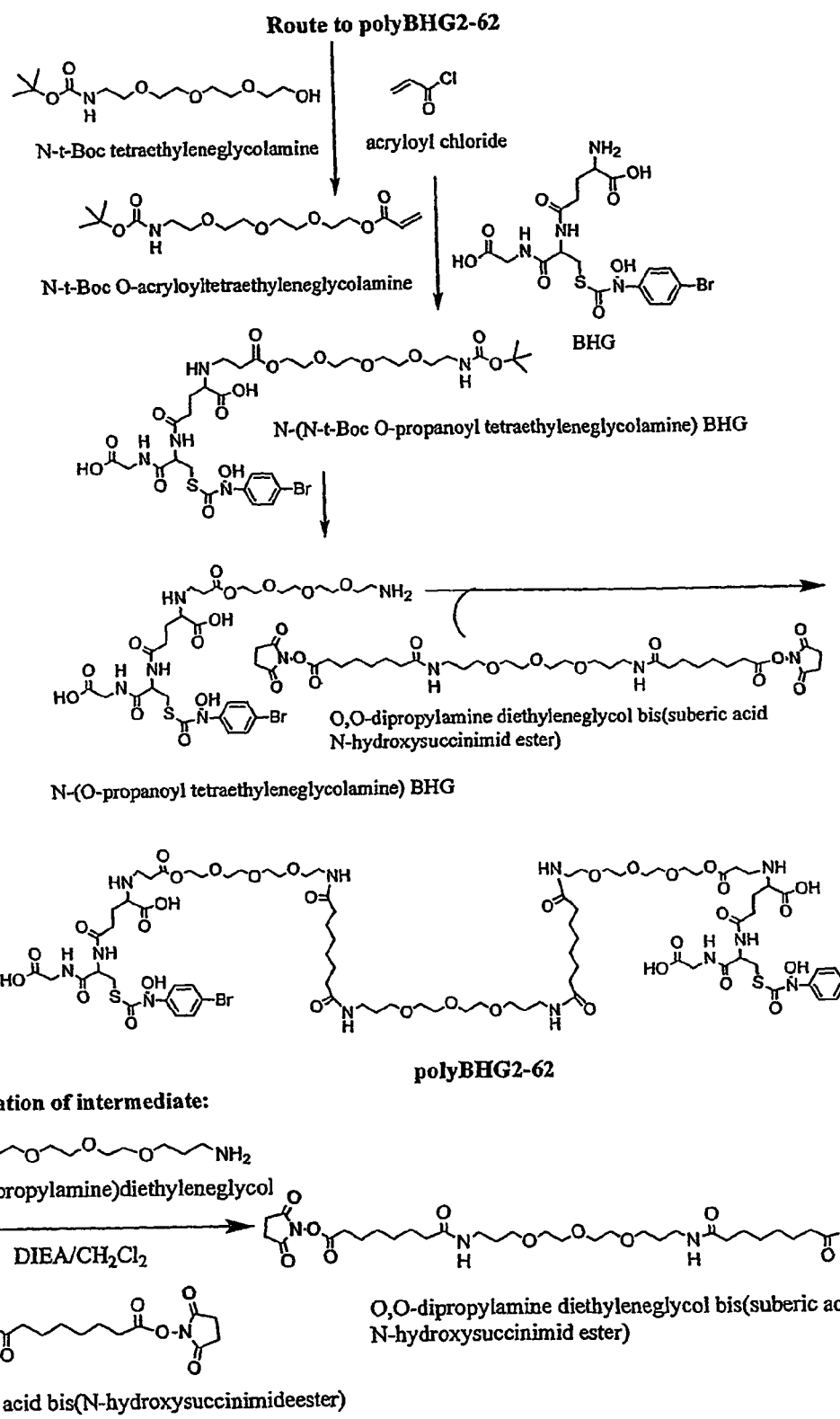
FIG. 2 shows a synthetic route to obtain bivalent transition state analogue N—(O-propanoyl tetraethyleneglycolamine O,O'-dipropylamine diethyleneglycol bis(suberic acid) S—(N-p-bromo-phenyl-N-hydroxycarbamoyl)glutathione (hereinafter polyBHG2-62) containing a mixed poly-ethyleneglycol/suberate diamide linker.
Figure 3:
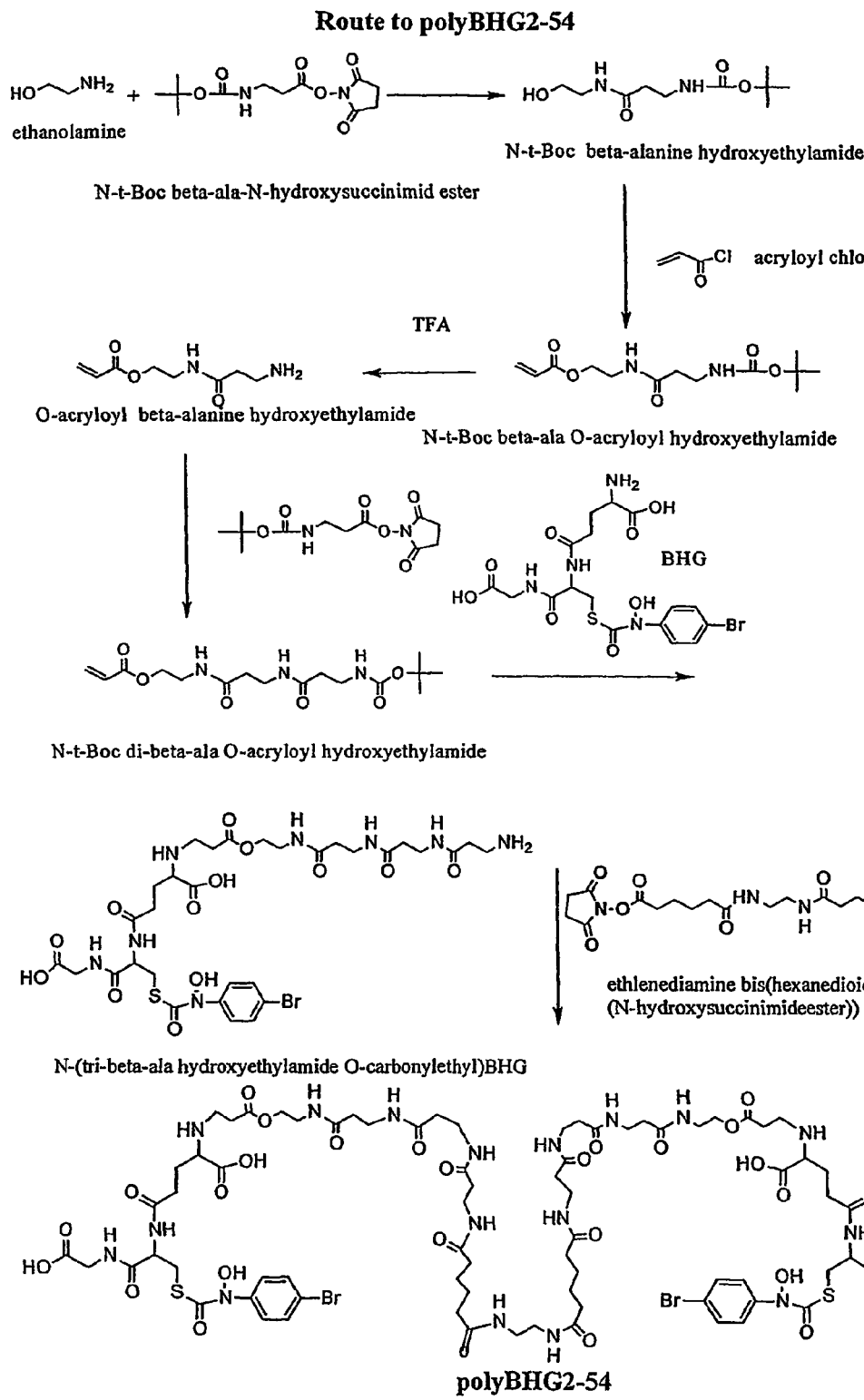
FIG. 3 shows a synthetic route to obtain bivalent transition state analogue N-(tri-beta-ala hydroxyethylamide ethylenediamine bis(hexanedioic acid O-carbonylethyl)S—(N-p-bromophenyl-N-hydroxy-carbamoyl)glutathione (hereinafter polyBHG2-54) containing a mixed poly-β-alanyl/hexanedioate diamide linker.
Figure 3:
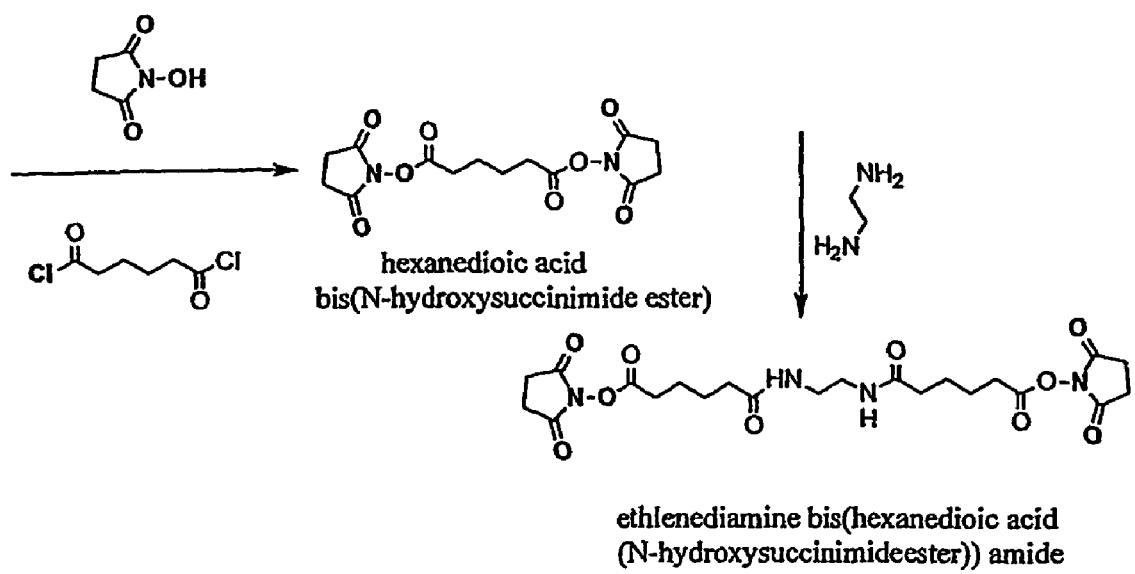

The synthetic routes used to generate bivalent competitive inhibitors of GlxI by cross-linking the reversible competitive inhibitor S-(4-bromophenyl-N-hydroxyphenyl)-glutathione (BHG) using the mixed poly-ethyleneglycol/suberate diamide linker is given in FIG. 2; that for synthesis of the corresponding bivalent inhibitor using the mixed poly-β-alanyl/hexanedioate diamide linker is given in FIG. 3.

Route to polyBHG2-62 (FIG. 2) N-t-Boc O-acryloyltetraethyleneglycolamine

To a solution of N-t-Boc tetraethyleneglycolamine (95 mg, 0.32 mmol) in 1 ml DMF plus 0.2 ml DIEA at 0° C. was added acryloyl chloride (32 µl). The reaction mixture was stirred for 30 min, the solvent was removed in vacuo and the residue fractionated by RP-HPLC using 25% acetonitrile in water containing 0.1% TFA as running solvent. The product peaks were collected, and the solvent removed to give 39 mg of product as a colorless liquid. Yield: 35%. $^1$H NMR (300 MHz, CD3OD, TMS as standard) δ6.37 (dd, J=17.2, 1.8 Hz, 1H), 6.18 (dd, J=17.2, 10.3 Hz, 1H), 5.90 (dd, J=10.3, 1.5 Hz, 1H), 4.29 (m, 2H), 3.74 (m, 2H), 3.65 (m, 8H), 3.50 (t, J=5.5 Hz, 2H), 3.21 (t, J=5.9 Hz, 2H), 1.43 (s, 9H).

N—(O-propanoyl tetraethyleneglycolamine) BHG

To a solution of BHG (117 mg, 0.22 mmol) in 1.5 ml DMF and 0.3 ml DIEA (diisopropylethylamine) maintained at 40° C. in a water bath was added N-t-Boc O-acryloyltetraethyleneglycolamine (39 mg, 0.11 mmol). After stirring the reaction mixture for 24 hours, the solvent was removed in vacuo and the residue fractionated by RP-HPLC using an initial isocratic elution with 25% acetonitrile in water, containing 0.1% TFA, followed by a linear gradient from 25% acetonitrile in water, containing 0.1% TFA, to 100% acetonitrile. The peaks corresponding to N—(N-t-Boc O-propanoyl tetraethyleneglycolamine) BHG were collected, the solvent removed and dried under vacuum overnight. $^1$H NMR (300 MHz, CD3OD, TMS as standard) δ7.57 (d, J=9.2 Hz, 2H), 7.52 (d, J=9.2 Hz, 2H), 4.66 (dd, J=8.4, 4.8 Hz, 1H), 4.29 (m, 2H), 4.06 (t, J=5.5 Hz, 1H), 3.94 (d, J=1.8 Hz, 2H), 3.73 (m, 2H), 3.63 (m, 8H), 3.49 (t, J=5.5 Hz, 2H), 3.36 (m, 3H), 3.21 (t, J=5.5 Hz, 2H), 3.11 (dd, J=14.3, 8.4 Hz, 1H), 2.83 (t, J=6.2 Hz, 2H), 2.63 (m, 2H), 2.24 (m, 2H), 1.43 (s, 9H). The residue was dissolved in 0.5 ml TFA, and stirred for 30 min. The TFA solution was fractionated by RP-HPLC using the same running solvent. The product peaks were pooled and dried under vacuum to give 9.2 mg final product: Yield 11% $^1$H NMR (300 MHz, CD$_3$OD, TMS as standard) δ7.57 (d, J=9.2 Hz, 2H), 7.52 (d, J=9.2 Hz, 2H), 4.64 (dd, J=8.4, 4.8 Hz, 1H), 4.29 (m, 2H), 4.05 (m, 1H), 3.95 (s, 2H), 3.66 (m, 12H), 3.36 (m, 3H), 3.11 (m, 3H), 2.84 (t, J=6.6 Hz, 2H), 2.63 (m, 2H), 2.24 (m, 2H).

O,O-Dipropylamine diethyleneglycol bis(suberic acid N-hydroxysuccinimide ester)

To a solution of suberic acid Bis(N-hydroxysuccinimideester (37 mg, 0.1 mmol) in 0.5 ml DMF was added 5.5 µl O,O-(dipropylamine)diethyleneglycol. Then the reaction mixture was stirred for 30 min and fractionated by RP-HPLC, using an initial isocratic elution with 25% acetonitrile in water, containing 0.1% TFA, followed by a linear gradient from 25% acetonitrile in water, containing 0.1% TFA, to 100% acetonitrile. The product peaks were collected, brought to dryness under vacuum to give 10.3 mg of the final product. Yield, 57% yield. $^1$H NMR (300 MHz, acetone-d$_6$, acetone 62.05) δ3.55 (m, 12H), 3.28 (m, 4H), 2.87 (s, 8H), 2.63 (t, J=7.3 Hz, 4H), 2.19 (m, 4H), 1.74 (m, 12H), 1.45 (m, 8H) BHG2-62

To a stirring solution of N—(O-propanoyl tetraethyleneglycolamine) BHG (4 mg, 0.005 mmol) in 0.2 ml DMF containing diethylamine (DIEA, 0.05 ml) was added O,O-dipropylamine diethyleneglycol bis(suberic acid N-hydroxysuccinimide ester) (1.9 mg, 0.0026 mmol). The reaction mixture was stirred for 30 min at room temperature. The reaction mixture was resolved by RP-HPLC using an initial isocratic elution with 25% acetonitrile in water, containing 0.1% TFA, followed by a linear gradient from 25% acetonitrile in water, containing 0.1% TFA, to 100% acetonitrile. The product peaks were collected and the solvent removed in vacuo to give the final product as a white solid (3.9 mg). Yield: 72%. $^1$H NMR (500 MHz, D$_2$O Tris buffer) δ 7.67 (d, J=8.3 Hz, 4H), 7.54 (d, J=8.3 Hz, 4H), 4.53 (m, 2H), 3.76 (m, 41H), 3.64 (m, 9H), 3.45 (t, J=5.2 Hz, 4H), 3.32 (t, J=6.7 Hz, 6H), 3.18 (m, 5H), 2.60 (m, 6H), 2.32 (m, 10H), 2.24 (m, 2H).

Route to polyBHG2-54 (FIG. 3) N-t-Boc β-ala O-acryloyl hydroxyethylamide

To N-t-Boc-β-Ala-N-hydroxysuccinimid ester (2 g, 7 mmol) in 10 ml of DMF at 0° C., was slowly added dropwise ethanolamine (850 μl, 14 mmol) and stirred for 30 min. The white precipitate was removed by filtration, and the filtrate was brought to dryness under vacuum to give the reaction intermediate t-Boc-β-Ala hydroxyethylamide as a light brown oil. $^1$H NMR (300 MHz, acetone-d$_6$, acetone (δ 2.05)): δ3.56 (t, J=5.5 Hz, 2H), 3.29 (m, 4H), 2.37 (t, J=7.0 Hz, 2H), 1.39 (s, 9H). The t-Boc-β-Ala hydroxyethylamide was dissolved in 15 ml of DMF plus 4 ml of DIEA at 0° C. and acryloyl chloride (704 μl) was slowly added dropwise. The reaction mixture stirred for 30 min, the solvent was removed under vacuum and the residue was dissolved in the running solvent composed of 20% acetonitrile in water containing 0.1% TFA gradient. The mixture was fractionated by RP-HPLC and the fractions containing the product were dried under to give 1.12 g of final product. Overall yield: 53% yield. $^1$H NMR (300 MHz, acetone-d$_6$, acetone (δ 2.05)), δ6.34 (dd, J=17.2, 1.5 Hz, 1H), 6.14 (dd, J=17.2, 10.3 Hz, 1H), 5.90 (dd, J=10.3, 1.5 Hz, 1H), 4.19 (t, J=5.5 Hz, 2H), 3.48 (m, 2H), 3.33 (m, 2H), 2.38 (t, J=6.6 Hz, 2H), 1.39 (s, 9H).

N-t-Boc di-β-ala O-acryloyl hydroxyethylamide

To N-t-Boc-β-ala O-acryloyl hydroxyethylamide (1.12 g, 3.9 mmol) was added 10 ml of TFA and the mixture was stirred at room temperature for 2 hours. The solvent was removed under vacuum and the residue was dissolved in 15 ml of DMF plus 5 ml of DIEA. To the reaction mixture was added N-t-Boc-β-Ala-N-hydroxysuccinimide ester (1.68 g, 5.9 mmol) and the mixture stirred over night at room temperature. The solvent was removed under vacuum and the residue fractionated by RP-HPLC using 50% acetonitrile in water containing 0.1% TFA as a running solvent. Overall yield: (0.77 g, 55%). $^1$H NMR (300 MHz, acetone-d$_6$, acetone (δ2.05)). Δ6.34 (dd, J=17.2, 1.8 Hz, 1H), 6.15 (dd, J=17.2, 10.6 Hz, 1H), 5.91 (dd, J=10.6, 1.8 Hz, 1H), 4.21 (t, J=5.5 Hz, 2H), 3.50 (m, 4H), 3.31 (m, 2H), 2.41 (m, 4H), 1.40 (s, 9H).

N-(di-β-ala hydroxyethylamide O-carbonylethyl) BHG

To a solution of BHG (0.56 g, 1.07 mmol) in 8 ml DMF plus 2 ml DIEA, was added N-t-Boc di-β-ala O-acryloylhydroxyethyl-amide (200 mg, 0.59 mmol). The reaction mixture was stirred at 45° C. for 48 hours, the solvent was removed in vacuo and the residue was fractionated by RP-HPLC using an initial isocratic elution with 25% acetonitrile in water, containing 0.1% TFA, followed by a linear gradient from 25% acetonitrile in water, containing 0.1% TFA, to 100% acetonitrile. The tubes containing the product were pooled, the was solvent evaporated, and the residue dissolved in 2 ml of TFA and incubated at room temperature for 1 hour. The TFA was removed under vacuum, the residue was dissolved in the running solvent, and then fractionated by RP-HPLC. Yield: 49 mg, 5.2%. $^1$H NMR (300 MHz, CD$_3$OD, TMS) δ 7.57 (d, J=9.2 Hz, 2H), 7.51 (d, J=9.2 Hz, 2H), 4.65 (dd, J=8.4, 4.8 Hz, 1H), 4.19 (t, J=5.5 Hz, 2H), 4.05 (t, J=5.5 Hz, 1H), 3.95 (s, 2H), 3.45 (m, 4H), 3.39 (t, J=6.2 Hz, 2H), 3.18 (t, J=6.6 Hz, 2H), 3.12 (m, 2H), 2.80 (m, 2H), 2.63 (m, 2H), 2.57 (t, J=6.2 Hz, 2H), 2.40 (t, J=6.6 Hz, 2H), 2.25 (m, 2H).

N-(tri-β-ala hydroxyethylamide O-carbonylethyl) BHG

To a solution of N-(di-β-ala hydroxyethylamine O-carbonylethyl) BHG (40 mg, 0.05 mmol) in 2 ml DMF plus 0.5 ml DIEA was added N-t-Boc-β-Ala-N-hydroxysuccinimid ester (29 mg, 0.1 mmol). The reaction mixture was stirred at room temperature overnight. The solvent was removed under vacuum and the residue dissolved in 1 ml TFA. After the solution was incubated for 1.5 hour, the TFA was removed under vacuum (rotatory evaporator) and the residue fractionated by RP-HPLC using an initial isocratic elution with 25% acetonitrile in water, containing 0.1% TFA, followed by a linear gradient from 25% acetonitrile in water, containing 0.1% TFA, to 100% acetonitrile. The product peaks were collected and brought to dryness under vacuum overnight to give 11 mg of final product. Yield: 25%. $^1$H NMR (500 MHz, D$_2$O, Tris buffer) δ7.67 (d, J=8.7 Hz, 2H), 7.54 (d, J=8.7 Hz, 2H), 4.73 (dd, J=8.5, 4.5 Hz, 1H), 4.26 (m, 1H), 3.86 (d, J=17.4 Hz, 1H), 3.84 (d, J=17.4 Hz, 1H), 3.72 (t, J=5.6 Hz, 2H), 3.65 (t, J=5.8 Hz, 1H), 3.52 (t, J=6.5 Hz, 4H), 3.43 (dd, J=14.6, 4.4 Hz, 1H), 3.40 (t, J=5.4 Hz, 2H), 3.20 (m, 4H), 2.63 (m, 4H), 2.54 (m, 6H), 2.25 (m, 2H).

polyBHG2-54

To a solution of N-(tri-β-ala hydroxyethylamide O-carbonylethyl)-BHG (10 mg, 0.012 mmol) in 0.5 ml DMF plus 0.15 ml DIEA was added ethylenediamine bis(hexanedioic acid (N-hydroxysuccinimideester)) amide (3 mg, 0.006 mmol). The reaction mixture was stirred for 30 min, the solvent was removed under vacuum and the residue fractionated by RP-HPLC using an initial isocratic elution with 25% acetonitrile in water, containing 0.1% TFA, followed by a linear gradient from 25% acetonitrile in water, containing 0.1% TFA, to 100% acetonitrile. The product peaks were pooled and dried under vacuum overnight to give 1.3 mg of final product. Yield, 11% yield. $^1$H NMR (500 MHz, D$_2$O Tris buffer) δ7.69 (d, J=8.7 Hz, 4H), 7.55 (d, J=8.7 Hz, 4H), 4.75 (dd, J=7.9, 4.12 Hz, 2H), 4.27 (m, 2H), 3.86 (d, J=17.3 Hz, 2H), 3.85 (d, J=17.3 Hz, 2H), 3.72 (m, 7H), 3.49 (m, 12H), 3.38 (m, 5H), 3.22 (m, 8H), 2.49 (m, 19H), 2.30 (m, 9H), 2.19 (m, 4H), 1.38 (m, 4H), 1.23 (m, 2H), 0.96 (m, 2H).

Hexanedioic Acid Bis(N-Hydroxysuccinimideester)

To a solution of N-hydroxysuccinimide (5 g, 42 mmol) in 100 ml of CH$_2$Cl$_2$ and 10 ml of DIEA at 0° C. was slowly added adipoyl chloride (3.94 g, 21 mmol). The reaction mixture was stirred for 30 min., the solvent was removed under vacuum. The residue was recrystalized from acetone to give 3.5 g of the desired product as white needlic crystals. Yield: 48%. $^1$H NMR (300 MHz, DMSO-d$_6$, TMS as standard) δ 2.79 (s, 8H), 2.72 (m, 4H), 1.70 (m, 4H).

Ethylenediamine bis(hexanedioic acid (N-hydroxysuccinimideester))amide

To a solution of hexanedioic acid bis(N-hydroxysuccinimideester) (272 mg, 0.8 mmol) in 2 ml DMF at room temperature, was added ethylenediamine (7.7 µl, 0.3 mmol). The reaction mixture was stirred for 30 min. and then fractionated by RP-HPLC, using 25% acetonitrile in water containing 0.1% TFA as running solvent. The product peaks were collected, brought to dryness under vacuum over overnight to give 9 mg of the desired product as a white solid. Yield 6%. $^1$H NMR (300 MHz, acetone-d$_6$, acetone δ2.05) δ3.27 (s, 4H), 2.88 (s, 8H), 2.66 (m, 4H), 2.21 (m, 4H), 1.72 (m, 8H).

Example 5

Competitive Inhibition Constants of Bivalent Inhibitors

Competitive inhibition constants ($K_i$s) of bivalent and monovalent enzyme inhibitors with human GlxI or yeast GlxI (yGlxI) were obtained from the change in the initial rates of product formation at various concentrations of the substrate in the presence or absence of the inhibitor. To a 1 ml cuvette containing 50 mM sodium phosphate buffer, pH 7.0, 0.5 mM EDTA, 25° C. and different concentrations of thiohemiacetal substrates with fixed concentrations of inhibitor was added approximately 0.02 U of enzyme. The initial rates of product formation were followed on the basis of the increase in absorbancy at 240 nm. Inhibition constants were obtained by fitting the initial rate data to the equation for competitive inhibition.

Figure 4:
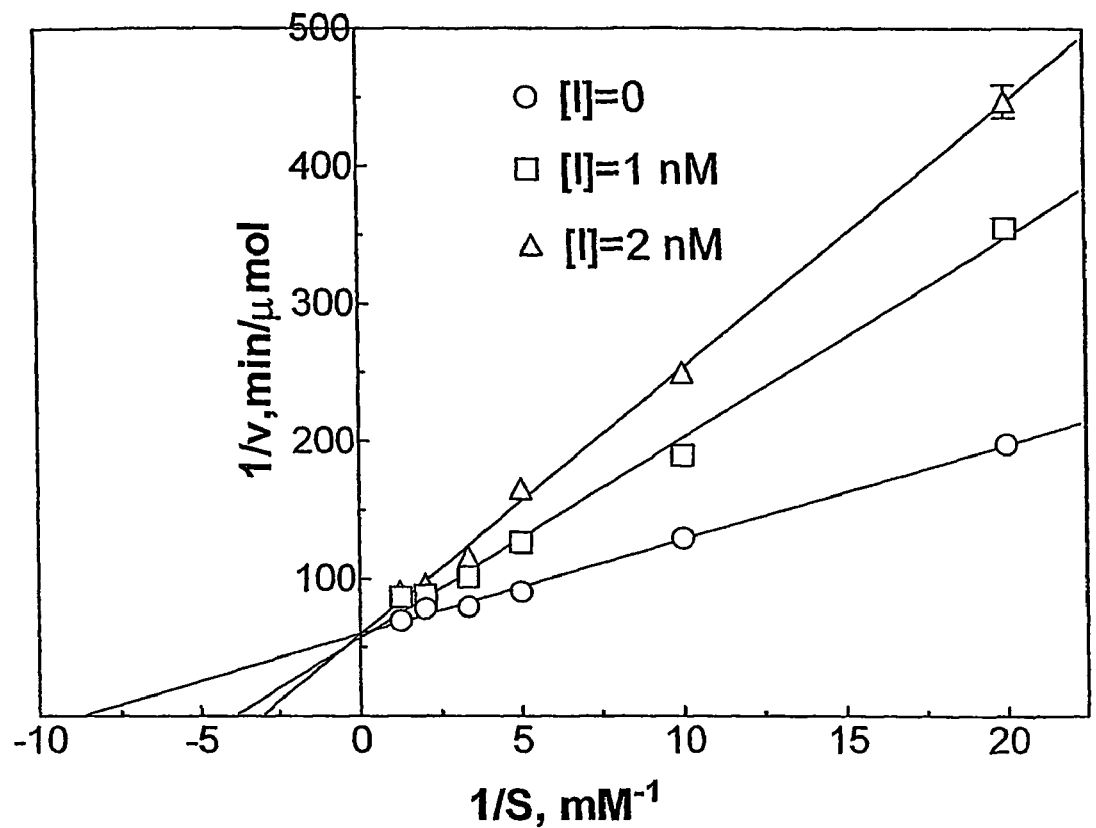
FIG. 4 shows a reciprocal plot of the initial rate of the hGlxI reaction versus concentration of GSH-methylglyoxal thiohemiacetal substrate (S) at different fixed concentrations of [CHG(β-alanyl)$_6$]$_2$ suberate diamide.
Figure 5:
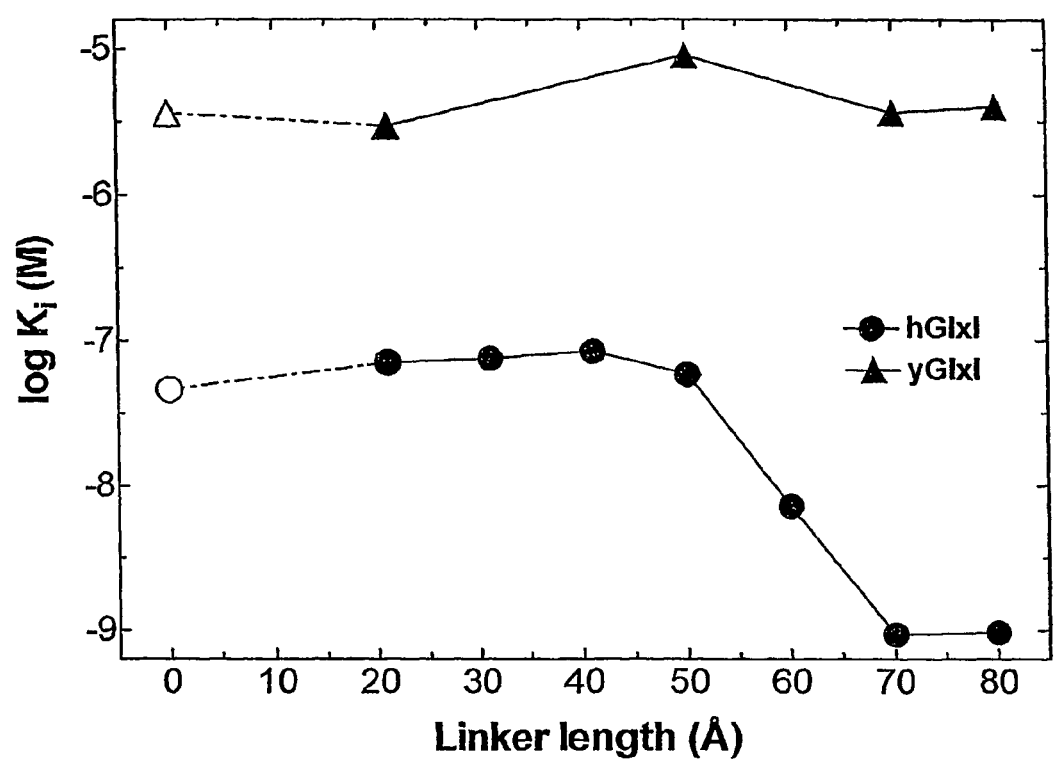
FIG. 5 shows a log plot of $K_i$ versus linker length for the bivalent inhibitors of Table 2 for human glyoxalase I (●) and yeast glyoxalase I (▲). Open symbols are for monovalent CHG.

The bivalent GlxI inhibitor (CHG-(β-alanyl)$_6$sub-CHG), shown in FIG. 1 proved to be a competitive inhibitor of hGlxI from human erythrocytes; e.g., FIG. 4. Further, model building of the inhibitors into the X-ray structure of hGlxI indicated that bivalent inhibitors with n≧4 may be capable of bridging the active sites. Indeed, a comparison of the competitive inhibition constants with linker length shows a dramatic increase in binding affinity when n=6 or 7, corresponding to linker lengths of 70 and 80 Angstroms, respectively; FIG. 5, Table 2.

TABLE 2

Competitive inhibition constants ($K_i$s) of CHG, CHG(β-ala)$_n$, and [CHG(β-Ala)$_n$]$_2$ suberate diamide with human GlxI (hGlxI), yeast GlxI (yGlxI) and bovine liver GlxII (bGlxII)[a]

| compound | linker length (Å) | $K_i$, hGlxI (nM)[b] | $K_i$, yGlxI (µM)[c] | $K_i$, bGlxII (nM)[c] |
|---|---|---|---|---|
| CHG | | 46 ± 4[d] | 3.6 ± 0.3[d] | 1700 ± 17 |
| CHG(β-Ala)$_n$, n = | | | | |
| 1 | 4 | 330 ± 6 | | 1200 ± 12 |
| 5 | 24 | 744 ± 39 | | |
| 6 | 30 | 583 ± 33 | | 870 ± 60 |
| [CHG(β-Ala)$_n$]$_2$sub., n = | | | | |
| 1 | 21 | 70.1 ± 1.3 | 3.0 ± 0.2 | 35 ± 4 |
| 2 | 31 | 75.9 ± 7.4 | | 50 ± 5 |
| 3 | 41 | 84.1 ± 2.4 | | |
| 4 | 50 | 59.6 ± 2.0 | 9.0 ± 0.3 | |
| 5 | 60 | 7.5 ± 0.5 | | |
| 6 | 70 | 0.96 ± 0.06 | 7.2 ± 0.1 | 142 ± 1 |
| 7 | 80 | 0.97 ± 0.02 | 4.1 ± 0.5 | 79 ± 8 |

[a]Conditions: Sodium phosphate buffer, 50 mM, pH 7, 25° C.
[b]Mean (±S.D.) for triplicate determinations
[c]Mean (±S.D.) for duplicate determinations
[d]Taken from Murthy et al, J. Med. Chem. 1994, 37 2161-2166.

Moreover, bivalent inhibitors that employed mixed polyethylene glycol/suberate diamide linkers, polyBHG2-62 (FIG. 2), and mixed poly-β-alanyl/hexanedioate diamide linkers, polyBHG2-54 (FIG. 3), also proved to be powerful competitive inhibitors of human GlxI with $K_i$ values of 1.0 and 0.3 nM respectively. Both linkers were about 60 Angstroms long.

Specificity of the Competitive Inhibitors

The bivalent inhibitors are highly specific for hGlxI versus other GSH-dependent enzymes, since the data does not show a dramatic increase in binding affinity between Yeast GlxI and bivalent inhibitors with increasing linker length Table 2. Thus, there is no evidence that binding of the longest bivalent inhibitor to yGlxI involves simultaneous binding to two active sites. Crosslinking has increased inhibitor selectivity by almost 100-fold, as CHG binds 78-fold more tightly to hGlxI than to yGlxI while [CHG(β-ala)$_6$]$_2$ suberate diamide binds about 7500-fold more tightly (Table 2).

For the thioester hydrolase bovine GlxII, the CHG(β-Ala)$_n$ monomers inhibit the enzyme as well as CHG (Table 2), indicating that the γ-glutamyl-NH$_2$ group of the bound inhibitor probably extends into bulk solvent and substituents at this position do not interfere with binding. In addition, there is no dramatic increase in binding affinity with increasing linker length, fully consistent with a single active site for GlxII. As observed with hGlxI, the affinity of the bivalent inhibitors for bGlxII is somewhat greater per CHG group (7-fold) than for CHG(β-Ala)$_6$ monomer. Comparing the inhibition constants of CHG and [CHG(β-Ala)$_6$]$_2$ suberate diamide for hGlxI versus bGlxII, crosslinking increases binding selectivity from 37-fold to 148-fold, a four-fold increase. Finally, the bivalent inhibitor [CHG-(β-ala)$_6$]$_2$ suberate diamide shows no inhibitory activity on GSH peroxidase or human placental GSH transferase up to an inhibitor concentration of 20 µM. Thus, the improved specificity of the bivalent inhibitors for hGlxI should reduce the side effects associated with the use of these compounds or pharmaceutical preparations thereof in cancer chemotherapy.

Example 6

In Vitro and In Vivo Efficacy Studies

In vitro efficacy: The inhibitors are examined for cytotoxicity using the MTT assay. Prostate cancer cells, PC3, DU145 and LNCaP are plated at 1×10$^3$ cells/well in 96 well culture plates. The cells are allowed 24 h to attach to the plates. At the end of 24 h the compounds are added to the culture plates. Typical ranges of final concentrations in the wells include: 100 µM, 30 µM, 10 µM, 3 µM, 1 µM, 0.3 µM and 0.1 µM for the initial assay. Each concentration is added to triplicate wells. Adjustments are made in the concentrations based on the results of the initial assay. At the end of 72 h of treatment, 50 µl of dye is added and the cells incubated for 4 h. At the end of the 4 h incubation, the plates are centrifuged and the media removed. DMSO (150 µl) is added to each well. The plates are shaken for approximately 20 min and read on a plate reader at 530 and 570 nm. The percent inhibition is calculated as (mean control $OD_{530}$–mean treated $OD_{530}$/control $OD_{530}$)×100=% Inhibition. The $IC_{50}$ is calculated using the Hill equation in the program ADAPT II. The assay is repeated 3 times with each cell line and the optimum concentrations to predict the $IC_{50}$.

In vivo efficacy in xenograft models of prostate cancer: Compounds exhibiting the lowest $IC_{50}$ values are evaluated in Es-1$^e$ C57Bl/6nu/nu mice bearing the most responsive prostate cancer xenografts, based on results of the in vitro assays. The first studies can determine the plasma pharmacokinetics of the agent after iv administration as a single dose, administered at its maximum tolerated dose on a q4d×3 schedule. Tissue distribution may also be measured, including the concentrations of the agent and potential metabolites in liver, kidney, spleen, heart, lung and tumor xenografts. Dosing is preferably by the intravenous route until bioavailability studies indicate good absorption by other routes. If the pharmacokinetic study indicates that adequate concentrations of the agent are present in the tumors, efficacy trials of the agent can be conducted. Agents showing a % T/C of 50% or less based on tumor volume are preferably evaluated in additional xenograft models of prostate cancer.

Determination of Efficacy: To determine efficacy, body weights and tumor volumes of each treatment group are measured twice weekly. The percentage of treated/control volumes (% T/C) is calculated by division of the median treated tumor volume by the median control tumor volume on each observation day and multiplication by 100. The optimal value (minimal value) obtained during the course of treatment is presented, and the day on which the optimal % T/C occurs is also be reported. Tumor growth delay is to be expressed as the percentage by which the treated-group median and/or tumor volume was delayed in achieving a specified tumor volume compared to the controls. The formula used is (T-C/C)×100, where T and C are the median time in days to reach a predetermined target tumor volume for the treated, and the control groups, respectively. Generally, the predetermined target is 600 mm$^3$ for slow growing tumors and 1,000 mm$^3$ for more rapidly growing tumors. The tumor doubling time is also calculated as the time required for the tumor volume to increase from 300 mm$^3$ to 600 mm$^3$. Net log cell kill is an estimate of the number of $log_{10}$ units of cells killed by the test agent and is calculated using the formula: {[(T-C)— duration of treatment]/doubling time}×0.301. At termination of the efficacy study, the exact tumor weights are measured by removal of the tumors, and the median and mean tumor weights between groups are also determined. The data from each treatment group on the efficacy trial will be analyzed using the statistical methods below.

PK Analysis: The clearance, steady-state volume of distribution, area under the curve from time zero to infinity, and terminal half-life are estimated by non-compartmental analysis with the LaGrange function as implemented by the LAGRAN computer program (Rocci and Jusko, *Comp. Methods Programs Biomed* 16: 203 (1983)). In addition, the individual concentrations of the drug detected in plasma versus time are fit to various compartment, open, linear models with the program ADAPT II (D'Argenio and Schumitzky, *Comp. Methods Programs Biomed*. 9, 115 (1979)) using either maximum likelihood or weighted least squares estimation. The most appropriate model are determined based on Akaike information criteria. Non-compartmental analysis are used to calculate the area under the concentration versus time curves from 0 to end of measurements (AUCp) or to infinity (AUC), volume of distribution at steady state ($V_{dss}$), and total body clearance ($CL_{tb}$). $CL_{tb}$=dose/AUC, and $V_{dss}$=dose×(AUMC/AUC), where AUMC is area under the moment curve from 0 to infinity. These calculations assume that less than 15% of the AUC is be estimated by exisiting data, which may not be the case for OPS measurements. Using compartmental analysis, intercompartmental rate constants and individual elimination and absorption rate constants are estimated. The best compartment model is chosen based upon Akaike criteria, where AIC=2p+n (1 n WSSR) where p is the number of parameters estimated in the chosen model, n is the number of data points, and WSSR is the weighted sum of squares residuals.

Data are analyzed by both parametric and nonparametric tests using the program, Minitab (Minitab, Inc., State College, Pa.). Group comparisons are done using ANOVA or Kruskall-Wallis tests. Pairwise comparisons are performed using Dunnett's test or the Mann-Whitney test. Significance is set at p≦0.05.

Any patents or publications referenced in this specification are indicative of the level of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent herein. The present examples along with the methods, procedures, treatments, molecules, and specific compounds described herein and other uses will occur to those skilled in the art that is encompassed within the spirit of the invention as defined by the scope of the claims.

What is claimed is:

1. A compound comprising:
   two human GlxI inhibitors covalently linked via a chemical linker, wherein each of said two human GlxI inhibitors, which may be the same or different, is an S-substituted glutathione or an S-substituted glutathione prodrug,
   wherein said GlxI inhibitors each have a γ-glutamyl amino group,
   wherein said chemical linker is covalently bound to each GlxI inhibitor via said γ-glutamyl amino group, and wherein said chemical linker comprises (β-Ala)$_{5-7}$ and has a length of at least 50 Angstroms.

2. The compound of claim 1, wherein said chemical linker has a length of at least 70 Angstroms.

3. The compound of claim 1, wherein at least one of said two human GlxI inhibitors is a reversible competitive inhibitor of human GlxI.

4. The compound of claim 3, wherein said reversible competitive inhibitor is an S—(N-aryl/alkyl-N-hydroxycarbamoyl)glutathione.

5. The compound of claim 3, wherein said reversible competitive inhibitor is selected from the group consisting of:
   S—(N-p-chlorophenyl-N-hydroxycarbamoyl)glutathione, S-(4-chlorophenyl-N-hydroxyphenyl)glutathione,
   S—(N-p-bromophenyl-N-hydroxycarbamoyl)glutathione, S-(4-bromophenyl-N-hydroxyphenyl)glutathione,
   S-(N-p-iodophenyl-N-hydroxycarbamoyl)glutathione,
   S-(N-phenyl-N-hydroxycarbamoyl)glutathione, S-p-bromobenzyl-glutathione,
S-(N-hydroxy-N-methylcarbamoyl)glutathione,
S-(N-methyl-N-hydroxycarbamoyl)glutathione,
S-(N-ethyl-N-hydroxycarbamoyl)glutathione,
S-(N-propyl-N-hydroxycarbamoyl)glutathione,
S-(N-butyl-N-hydroxycarbamoyl)glutathione,
S-(N-pentyl-N-hydroxycarbamoyl)glutathione, and
S-(N-hexyl-N-hydroxycarbamoyl)glutathione.

6. The compound of claim 1, wherein at least one of said two human GlxI inhibitors is an irreversible inactivator of human GlxI.

7. The compound of claim 6, wherein said irreversible inactivator of human GlxI is S-(bromoacetoxy butyl acetoxy) glutathione or S-(bromoacetoxy propyl acetoxy)glutathione.

8. The compound of claim 1, wherein said prodrug is selected from the group consisting of a di- or mono-ethyl ester S-substituted glutathione prodrug, a di- or mono-n-propyl ester S-substituted glutathione prodrug, a di- or mono-isopropyl ester S-substituted glutathione prodrug, and a di- or mono-cyclopentyl ester S-substituted glutathione prodrug.

9. The compound of claim 1, wherein at least one of said two human GlxI inhibitors is hydrolyzed by human GlxII.

10. A compound represented by the formula:

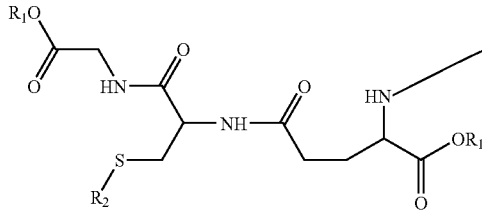
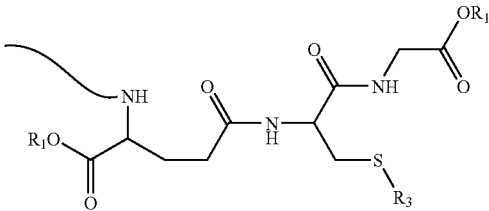

where L is a chemical linker represented by the formula $(Z_1)_a$—$(Z_2)_b$—$(Z_3)_c$, wherein $Z_1$, $Z_2$, and $Z_3$, which may be the same or different, are each selected from the group consisting of:
$C(O)(CH_2)_d NH$,
$CO(CH_2)_e C(O)$,
$(CH_2CH_2)_f NHC(O)$,
$(CH_2CH_2)_g C(O)NH$,
$(CH_2)_h C(O)(OCH_2CH_2)_i NHC(O)(CH_2)_j C(O)$,
$NH(CH_2)_k (OCH_2CH_2)_l$—$O(CH_2)_m NH$,
$(CH_2)_n C(O)(OCH_2CH_2)_o NH(C(O)(CH_2)_p N_q C(O)$-alkyl,
and $C(O)NH(CH_2)_r NHC(O)$—$(CH_2)_s C(O)(NHCH_2CH_2)_t NH(C(O)(CH_2)_u NH)_v C(O)$-alkyl; wherein subscripts a through v are independently 1-20;

wherein $R_1$ is hydrogen or a member selected from the group consisting of:
(1) an alkyl($C_1$-$C_{18}$) optionally substituted with a halogen or arylalkyl ($C_6$-$C_{20}$);
(2) a cycloalkyl($C_3$-$C_8$) optionally substituted with a halogen, alkyl($C_1$-$C_{18}$) or arylalkyl($C_6$-$C_{20}$);
(3) a cycloalkenyl($C_5$-$C_7$) optionally substituted with a halogen, alkyl($C_1$-$C_{18}$) or arylalkyl($C_6$-$C_{20}$); and
(4) an aryl($C_6$-$C_{20}$) optionally substituted with a halogen, alkyl($C_1$-$C_{18}$) or arylalkyl ($C_6$-$C_{20}$);

wherein $R_2$ and $R_3$, which may be the same or different, are each selected from the group consisting of:
(1) an alkyl($C_1$-$C_{18}$) optionally substituted with a halogen or arylalkyl($C_6$-$C_{20}$);
(2) a cycloalkyl($C_3$-$C_{18}$) optionally substituted with a halogen, alkyl($C_1$-$C_{18}$) or arylalkyl($C_6$-$C_{20}$);
(3) a cycloalkenyl($C_5$-$C_7$) optionally substituted with a halogen, alkyl($C_1$-$C_{18}$) or arylalkyl($C_6$-$C_{20}$); and
(4) an aryl($C_6$-$C_{20}$) optionally substituted with a halogen, alkyl($C_1$-$C_{18}$) or arylalkyl ($C_6$-$C_{20}$).

11. The compound of claim 10, wherein $R_2$ and $R_3$, which may be the same or different, are each selected from the group consisting of:
(1) an alkyl($C_6$-$C_{10}$) optionally substituted with a halogen or arylalkyl(C6-$C_{10}$);
(2) a cycloalkyl($C_3$-$C_8$) optionally substituted with a halogen, alkyl($C_1$-$C_6$) or arylalkyl($C_6$-$C_{10}$);
(3) a cycloalkenyl($C_6$-$C_7$) optionally substituted with a halogen, alkyl($C_1$-$C_6$) or arylalkyl($C_6$-$C_{10}$); and
(4) aryl($C_6$-$C_{12}$) optionally substituted with a halogen, alkyl($C_1$-$C_6$) or arylalkyl ($C_6$-$C_{10}$).

12. A compound represented by the formula:

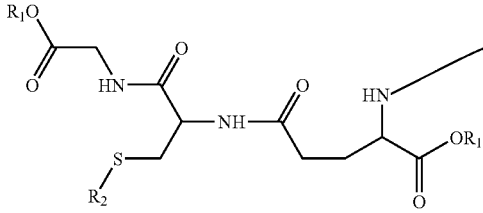
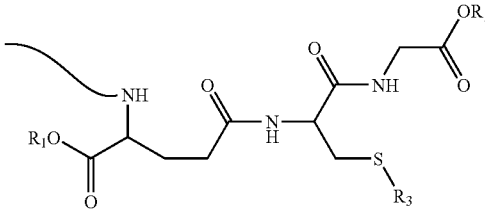

where L is a chemical linker represented by the formula $(Z_1)_a$—$(Z_2)_b$—$(Z_3)_c$, wherein $Z_1$, $Z_2$, and $Z_3$, which may be the same or different, are each selected from the group consisting of:
$C(O)(CH_2)_d NH$,
$CO(CH_2)_e C(O)$,
$(CH_2CH_2)_f NHC(O)$, $(CH_2CH_2)_g$—C(O)NH,
$(CH_2)_hC(O)(OCH_2CH_2)_iNHC(O)(CH_2)_jC(O)$,
$NH(CH_2)_k(OCH_2CH_2)_l$—$(CH_2)_mNH$,
$(CH_2)_nC(O)(OCH_2CH_2)_oNHC(O)(CH_2)_pN_qC(O)$-alkyl,
and $C(O)NH(CH_2)_rNHC(O)$—$(CH_2)_sC(O)(NHCH_2CH_2)_t\ NH(C(O)(CH_2)_uNH)_vC(O)$alkyl; wherein subscripts a through v are independently 1-20;
wherein $R_1$ is hydrogen or a member selected from the group consisting of:
(1) an alkyl($C_1$-$C_{18}$) optionally substituted with a halogen or arylalkyl ($C_6$-$C_{20}$);
(2) a cycloalkyl($C_3$-$C_8$) optionally substituted with a halogen, alkyl($C_1$-$C_{18}$) or arylalkyl($C_6$-$C_{20}$);
(3) a cycloalkenyl($C_5$-$C_7$) optionally substituted with a halogen, alkyl($C_1$-$C_{18}$) or arylalkyl($C_6$-$C_{20}$); and
(4) an aryl($C_6$-$C_{20}$) optionally substituted with a halogen, alkyl($C_1$-$C_{18}$) or arylalkyl ($C_6$-$C_{20}$);
wherein $R_2$ and $R_3$, which may be the same or different, are each selected from the group consisting of:
—$R_6C(O)X(R_4)X_1C(O)Y$, wherein $R_6$ is alkylene ($C_1$-$C_6$) or arylene ($C_6$-$C_{20}$); X and $X_1$, which may be the same or different, are O, N, or C; $R_4$ is selected from the group consisting of alkylene ($C_1$-$C_{20}$), (poly) ethylene glycol $(CH_2CH_2O)_{1-20}$, (poly)ethylene amine $(CH_2CH_2ON)_{1-20}$, and arylene ($C_6$-$C_{20}$); and Y is halomethylene or alkenyl($C_1$-$C_{20}$);
—$C(O)N(OH)X(R_4)X_1C(O)Y$, wherein X and $X_1$, which may be the same or different, are O, N, or C; $R_4$ is selected from the group consisting of alkylene ($C_1$-$C_{20}$), (poly) ethylene glycol $(CH_2CH_2O)_{1-20}$, (poly)ethylene amine $(CH_2CH_2ON)_{1-20}$, and arylene ($C_6$-$C_{20}$); and Y is halomethylene or alkenyl($C_1$-$C_{20}$), and
—$C(O)X(R_4)X_1C(O)Y$, wherein X and $X_1$, which may be the same or different, are O, N, or C; $R_4$ is selected from the group consisting of alkylene ($C_1$-$C_{20}$), (poly) ethylene glycol $(CH_2CH_2O)_{1-20}$, (poly)ethylene amine $(CH_2CH_2ON)_{1-20}$, and arylene ($C_6$-$C_{20}$); and Y is halomethylene or alkenyl($C_1$-$C_{20}$).

13. The compound of claim 12, wherein $R_1$ is hydrogen or a member selected from the group consisting of:
(1) an alkyl($C_1$-$C_8$) optionally substituted with a halogen or arylalkyl($C_6$-$C_{20}$);
(2) a cycloalkyl($C_3$-$C_8$) optionally substituted with a halogen, alkyl($C_1$-$C_{10}$) or arylalkyl($C_6$-$C_{20}$);
(3) a cycloalkenyl($C_5$-$C_7$) optionally substituted with a halogen, alkyl($C_1$-$C_{10}$) or arylalkyl($C_6$-$C_{20}$); and
(4) an aryl($C_6$-$C_{10}$) optionally substituted with a halogen, alkyl($C_1$-$C_{10}$) or arylalkyl ($C_6$-$C_{20}$);
wherein $R_2$ and $R_3$, which may be the same or different, are each selected from the group consisting of:
—$R_6C(O)X(R_4)X_1C(O)Y$, wherein $R_6$ is alkylene ($C_3$-$C_6$) or arylene ($C_6$-$C_{12}$); X and $X_1$, which may be the same or different, are O, N, or C; $R_4$ is selected from the group consisting of alkylene ($C_1$-$C_{10}$), (poly) ethylene glycol $(CH_2CH_2O)_{1-10}$, (poly)ethylene amine $(CH_2CH_2ON)_{1-10}$, and arylene ($C_6$-$C_{12}$); and Y is halomethylene or alkenyl($C_1$-$C_{10}$);
—$C(O)N(OH)X(R_4)X_1C(O)Y$, wherein X and $X_1$, which may be the same or different, are O, N, or C; $R_4$ is selected from the group consisting of alkylene ($C_3$-$C_{10}$), (poly) ethylene glycol $(CH_2CH_2O)_{1-10}$, (poly)ethylene amine $(CH_2CH_2ON)_{1-10}$, and arylene ($C_6$-$C_{12}$); and Y is halomethylene or alkenyl($C_1$-$C_{10}$), and
—$C(O)X(R_4)X_1C(O)Y$, wherein X and $X_1$, which may be the same or different, are O, N, or C; $R_4$ is selected from the group consisting of alkylene ($C_3$-$C_{10}$), (poly) ethylene glycol $(CH_2CH_2O)_{1-10}$, (poly)ethylene amine $(CH_2CH_2ON)_{1-10}$, and arylene ($C_6$-$C_{12}$); and Y is halomethylene or alkenyl($C_1$-$C_{10}$).

14. The compound of claim 12,
wherein $R_1$ is H or ethyl,
wherein $R_2$ and $R_3$, which are the same, are —$C(O)N(OH)C_6H_4Cl$ or —$C(O)N(OH)C_6H_4Br$, and
wherein L is $(C(O)C_2H_4NH)_nC(O)C_6H_{12}C(O)(NHC_2H_4C(O))$—, wherein n is 6 or 7.

15. An S-substituted glutathione or S-substituted glutathione prodrug represented by the formula: S—$(CH_2C(O)OROC(O)CH_2X)$glutathione, wherein R is selected from the group consisting of alkylene ($C_1$-$C_{20}$), polyethylene glycol $(CH_2CH_2O)_{1-20}$, polyethylene amine $(CH_2CH_2N)_{1-20}$, and arylene ($C_6$-$C_{20}$), and wherein X is a halogen.

16. The compound of claim 15, wherein said S-substituted glutathione is S-(bromoacetoxy butyl acetoxy)glutathione or S-(bromoacetoxy propyl acetoxy)glutathione.

17. A pharmaceutical composition comprising the compound of claim 1 and a pharmaceutically acceptable carrier.

18. A pharmaceutical composition comprising the compound of claim 15 and a pharmaceutically acceptable carrier.

19. The pharmaceutical composition of claim 17, wherein said pharmaceutically acceptable carrier is aqueous isopropyl-β-cyclodextran.

20. The pharmaceutical composition of claim 18, wherein said pharmaceutically acceptable carrier is aqueous isopropyl-β-cyclodextran.

21. A method of treating a neoplastic condition in a subject, comprising administering to a subject in need of such treatment a pharmaceutically effective amount of the composition of claim 17.

22. A method of treating a neoplastic condition in a subject, comprising administering to the subject in need of such treatment a pharmaceutically effective amount of the composition of claim 18.

23. The method of claim 21, wherein said pharmaceutically effective amount is a dose of from 0.1 mg/kg to about 5 mg/kg.

24. The method of claim 22, wherein said pharmaceutically effective amount is a dose of from 0.1 mg/kg to about 5 mg/kg.

25. The method of claim 21, wherein said neoplastic condition is selected from the group consisting of breast cancer, ovarian cancer, prostate cancer, lung cancer, colon cancer, kidney cancer, liver cancer, brain cancer, and haemopoetic tissue cancer.

26. The method of claim 22, wherein said neoplastic condition is selected from the group consisting of breast cancer, ovarian cancer, prostate cancer, lung cancer, colon cancer, kidney cancer, liver cancer, brain cancer, and haemopoetic tissue cancer.

27. A method of inhibiting the proliferation of a tumor cell comprising contacting a tumor cell with an amount of the compound of claim 1 effective to inhibit proliferation of said tumor cell.

28. A method of inhibiting the proliferation of a tumor cell comprising contacting a tumor cell with an amount of the compound of claim 15 effective to inhibit proliferation of said tumor cell.

* * * * *